United States Patent
Jackson et al.

(10) Patent No.: US 12,193,851 B2
(45) Date of Patent: Jan. 14, 2025

(54) VENTED ENDOSCOPE TRAY COVERS, SYSTEMS AND METHODS

(71) Applicant: Medivators Inc., Minneapolis, MN (US)

(72) Inventors: Mark Jackson, Great Wakering (GB); Joshua J. Korth, St. Louis Park, MN (US)

(73) Assignee: Medivators Inc., Minneapolis, MN (US)

( * ) Notice: Subject to any disclaimer, the term of this patent is extended or adjusted under 35 U.S.C. 154(b) by 421 days.

(21) Appl. No.: 17/435,910

(22) PCT Filed: Feb. 25, 2020

(86) PCT No.: PCT/US2020/019640
§ 371 (c)(1),
(2) Date: Sep. 2, 2021

(87) PCT Pub. No.: WO2020/190459
PCT Pub. Date: Sep. 24, 2020

(65) Prior Publication Data
US 2022/0211458 A1  Jul. 7, 2022

Related U.S. Application Data

(60) Provisional application No. 62/820,483, filed on Mar. 19, 2019.

(51) Int. Cl.
*A61L 2/26* (2006.01)
*A61B 1/00* (2006.01)
(Continued)

(52) U.S. Cl.
CPC .......... *A61B 50/33* (2016.02); *A61B 1/00144* (2013.01); *A61B 2050/006* (2016.02);
(Continued)

(58) Field of Classification Search
CPC ..... A61B 1/00144; A61B 50/33; A61B 50/13; A61B 50/30; A61B 50/36;
(Continued)

(56) References Cited

U.S. PATENT DOCUMENTS

| 803,102 A | 10/1905 | Harris |
|---|---|---|
| 1,592,726 A | 7/1926 | Dunbar |

(Continued)

FOREIGN PATENT DOCUMENTS

| AU | 2018211256 A1 | 2/2019 |
|---|---|---|
| CN | 108030556 A | 5/2018 |

(Continued)

OTHER PUBLICATIONS

ARES flexible endoscope automated reprocessing system (Steelco) Jul. 12, 2018 (Jul. 12, 2018) [retreived from the internet on Aug. 24, 2020 (Aug. 24, 2020) at https://web.archive.org/web/20180712214831/ http://www.peacocks.net/_filecache/9e4/a6e/550-steelco-ares-rev04. pdf].

(Continued)

*Primary Examiner* — Gideon R Weinerth

(57) ABSTRACT

A cover for an endoscope storage tray is provided. The cover comprises a flexibly deformable material substantially impermeable to fluids. The flexibly deformable material is configured to be temporarily secured to the tray so as to cover an endoscope storage compartment of the tray. A one-way valve is attached to the cover that is configured to release air flowing from the endoscope storage compartment of the tray to the cover. Systems and methods are also provided.

19 Claims, 18 Drawing Sheets

(51) Int. Cl.
*A61B 50/33* (2016.01)
*A61L 2/20* (2006.01)
*A61B 50/00* (2016.01)
*A61B 50/30* (2016.01)
*A61B 90/70* (2016.01)

(52) U.S. Cl.
CPC ......... *A61B 50/30* (2016.02); *A61B 2090/701* (2016.02); *A61L 2202/24* (2013.01)

(58) Field of Classification Search
CPC .......... A61B 2090/701; A61B 1/00142; A61B 1/00131; A61B 1/00147; A61B 2050/314; A61B 2050/0057; A61B 2050/005; A61B 2050/006; A61B 2050/3007; A61B 2050/0065; A61B 2050/002; A61L 2202/24; A61L 2202/18; A61L 2202/122
USPC .... 206/223, 368, 369, 63.5, 363; 220/367.1; 426/396, 129, 418, 316; 422/292, 33, 40; 383/100
See application file for complete search history.

(56) References Cited

U.S. PATENT DOCUMENTS

| | | | |
|---|---|---|---|
| 1,717,974 A | 6/1929 | Heinrichs | |
| 2,080,108 A | 5/1937 | Bradstein | |
| 2,214,946 A | 9/1940 | Werner | |
| 2,412,325 A | 12/1946 | Devine et al. | |
| 3,157,902 A | 11/1964 | Hardwick | |
| 3,757,990 A | 9/1973 | Buth | |
| 3,770,119 A | 11/1973 | Hultberg et al. | |
| 3,949,934 A * | 4/1976 | Goglio | B65D 77/225 426/118 |
| 4,042,109 A | 8/1977 | Barcan | |
| 4,053,280 A | 10/1977 | Salisbury | |
| 4,256,225 A * | 3/1981 | Jackson | B65D 85/00 206/363 |
| 4,466,552 A | 8/1984 | Butterworth et al. | |
| 4,574,978 A | 3/1986 | Hodges | |
| 4,583,643 A * | 4/1986 | Sanderson | B65D 81/2023 383/44 |
| 4,704,254 A * | 11/1987 | Nichols | A61L 2/26 422/26 |
| 4,730,729 A * | 3/1988 | Monch | A61B 50/30 206/370 |
| 4,750,619 A | 6/1988 | Cohen et al. | |
| 4,754,595 A | 7/1988 | Sanderson | |
| 4,903,718 A * | 2/1990 | Sullivan | A61C 19/002 383/41 |
| 4,948,266 A | 8/1990 | Bencic | |
| 5,108,195 A | 4/1992 | Perron | |
| 5,207,325 A | 5/1993 | Kennedy | |
| 5,263,777 A * | 11/1993 | Domke | B65D 77/225 426/118 |
| 5,288,467 A * | 2/1994 | Biermaier | A61L 2/26 422/116 |
| 5,295,606 A | 3/1994 | Karwoski | |
| 5,392,917 A | 2/1995 | Alpern et al. | |
| 5,409,126 A | 4/1995 | Demars | |
| 5,443,801 A * | 8/1995 | Langford | A61L 11/00 422/294 |
| 5,733,243 A * | 3/1998 | Yabe | A61B 1/012 600/156 |
| 5,882,589 A | 3/1999 | Mariotti | |
| 5,989,608 A * | 11/1999 | Mizuno | B65D 77/225 426/118 |
| 6,029,844 A | 2/2000 | Brady | |
| 6,041,794 A * | 3/2000 | Lin | A61L 2/18 134/22.12 |
| 6,139,185 A | 10/2000 | Hamilton et al. | |
| 6,151,910 A | 11/2000 | Hazen | |
| 6,210,638 B1 | 4/2001 | Grieco et al. | |
| 6,235,692 B1 | 5/2001 | Scoville et al. | |
| 6,305,567 B1 | 10/2001 | Sulpizio | |
| 6,312,645 B1 * | 11/2001 | Lin | A61B 1/121 422/294 |
| 6,378,721 B1 | 4/2002 | Williams | |
| 6,380,524 B1 * | 4/2002 | Keller | B65D 77/225 426/118 |
| 6,622,862 B1 * | 9/2003 | Corrado | A61L 2/26 422/300 |
| 6,622,864 B1 | 9/2003 | Debbs et al. | |
| 6,641,781 B2 * | 11/2003 | Walta | A61B 50/10 134/92 |
| 6,733,803 B1 * | 5/2004 | Vidkjaer | B65D 77/225 426/62 |
| 6,749,063 B2 | 6/2004 | Parker | |
| 6,916,456 B2 * | 7/2005 | Martineau | A61B 1/123 134/169 C |
| 6,994,823 B2 * | 2/2006 | Hight, III | A61B 1/121 422/1 |
| 7,041,941 B2 | 5/2006 | Faries, Jr. et al. | |
| D531,734 S | 11/2006 | Haunschild et al. | |
| 7,132,089 B2 * | 11/2006 | Lacabanne | A61L 2/24 206/436 |
| 7,178,555 B2 * | 2/2007 | Engel | B65D 77/225 426/118 |
| 7,476,368 B2 * | 1/2009 | Sargent | A61L 2/28 422/301 |
| 7,630,791 B2 | 12/2009 | Nguyen et al. | |
| 7,993,602 B2 * | 8/2011 | Moriyama | A61L 2/26 422/292 |
| 8,287,816 B2 * | 10/2012 | Kral | A61B 50/13 422/1 |
| 8,414,471 B2 * | 4/2013 | Mandava | A61B 1/00059 600/102 |
| 8,435,445 B2 | 5/2013 | Kral | |
| 8,454,901 B1 | 6/2013 | Snyder, III | |
| 8,733,551 B2 | 5/2014 | Parker et al. | |
| 8,747,739 B2 * | 6/2014 | Parker | A61B 50/00 422/294 |
| 8,795,603 B2 | 8/2014 | Ghelman et al. | |
| 8,851,287 B2 | 10/2014 | Becklin | |
| 8,905,258 B2 * | 12/2014 | Javid | B65D 41/22 229/87.08 |
| 9,348,013 B2 | 5/2016 | Rahim et al. | |
| 9,703,264 B2 | 7/2017 | Freijsen et al. | |
| 9,910,965 B2 | 3/2018 | Bufalini et al. | |
| D818,841 S * | 5/2018 | Newton | D9/702 |
| D819,409 S * | 6/2018 | Newton | D7/554.3 |
| 10,405,938 B2 | 9/2019 | Ramsey | |
| 10,418,831 B2 | 9/2019 | Racenet et al. | |
| 10,456,494 B2 | 10/2019 | Roudebush et al. | |
| 10,463,441 B2 * | 11/2019 | Tate | H05K 5/0213 |
| D909,883 S * | 2/2021 | Newton | D9/702 |
| D921,490 S * | 6/2021 | Newton | D9/702 |
| 11,445,900 B2 * | 9/2022 | King | A61B 1/125 |
| 11,696,811 B2 * | 7/2023 | Dalena | A61B 50/33 206/363 |
| 11,974,721 B2 * | 5/2024 | Jackson | A61B 50/33 |
| 2003/0078472 A1 * | 4/2003 | Parker | A61B 50/30 600/102 |
| 2004/0101456 A1 * | 5/2004 | Kuroshima | A61L 2/26 422/26 |
| 2005/0260097 A1 * | 11/2005 | Williams | A61L 2/206 422/28 |
| 2006/0193761 A1 * | 8/2006 | Moriyama | A61L 2/26 422/26 |
| 2007/0215507 A1 | 9/2007 | Glenn et al. | |
| 2007/0228080 A1 | 10/2007 | Lin et al. | |
| 2008/0251102 A1 | 10/2008 | Haack et al. | |
| 2009/0091453 A1 | 4/2009 | Ishida et al. | |
| 2009/0104094 A1 * | 4/2009 | Affaitati | A61L 2/24 422/295 |
| 2009/0123333 A1 * | 5/2009 | Parker | A61L 2/208 422/40 |
| 2009/0206674 A1 | 8/2009 | Noguchi et al. | |
| 2009/0261549 A1 * | 10/2009 | Kral | A61B 50/10 280/47.35 |

(56) References Cited

U.S. PATENT DOCUMENTS

| | | |
|---|---|---|
| 2010/0176016 A1 | 7/2010 | Pell |
| 2010/0189598 A1* | 7/2010 | Fraundorfer ............ A61L 2/186 |
| | | 422/292 |
| 2011/0002811 A1 | 1/2011 | Dane et al. |
| 2011/0192744 A1* | 8/2011 | Parker .................... A61B 50/30 |
| | | 206/363 |
| 2012/0152289 A1* | 6/2012 | Smith ...................... A61L 2/26 |
| | | 134/109 |
| 2013/0019910 A1 | 1/2013 | Ledel |
| 2013/0105344 A1* | 5/2013 | Hartley ............... A61B 1/00144 |
| | | 206/363 |
| 2013/0192647 A1 | 8/2013 | Ledel et al. |
| 2014/0069841 A1 | 3/2014 | Pizzato et al. |
| 2014/0083886 A1 | 3/2014 | Winterrowd et al. |
| 2014/0182629 A1 | 7/2014 | Dromard et al. |
| 2014/0270583 A1 | 9/2014 | Anderson |
| 2014/0339114 A1 | 11/2014 | Griffin |
| 2014/0353203 A1 | 12/2014 | Hu et al. |
| 2015/0257632 A1* | 9/2015 | Ramsey ............... B65D 81/267 |
| | | 206/204 |
| 2015/0259122 A1* | 9/2015 | Parker .................... B65B 31/04 |
| | | 53/410 |
| 2015/0272680 A1* | 10/2015 | Suzuki ............... A61B 1/00131 |
| | | 206/363 |
| 2016/0058900 A1 | 3/2016 | Sato |
| 2016/0081540 A1* | 3/2016 | Suzuki ............... A61B 1/00059 |
| | | 134/56 R |
| 2016/0095508 A1* | 4/2016 | Terliuc ............... A61B 1/00057 |
| | | 134/21 |
| 2016/0249915 A1 | 9/2016 | Beckman et al. |
| 2017/0056122 A1* | 3/2017 | Ramsey .................. A61B 50/36 |
| 2017/0091389 A1 | 3/2017 | Dukatz |
| 2017/0172397 A1* | 6/2017 | Zardini .................. A61B 1/125 |
| 2018/0028703 A1 | 2/2018 | McLaughlin et al. |
| 2018/0071045 A1 | 3/2018 | Cohen et al. |
| 2018/0134453 A1 | 5/2018 | Wassenburg |
| 2019/0021806 A1* | 1/2019 | Turbett .................. A61B 46/40 |
| 2019/0365500 A1 | 12/2019 | Erdmann et al. |
| 2019/0388181 A1* | 12/2019 | Petersen ............... A46B 9/026 |
| 2020/0118674 A1* | 4/2020 | Le .......................... A61B 50/10 |
| 2020/0187767 A1 | 6/2020 | Kramer et al. |
| 2020/0205925 A1* | 7/2020 | Cummings ............ B65D 25/16 |
| 2020/0315731 A1 | 10/2020 | Zardini et al. |
| 2021/0076923 A1 | 3/2021 | Awau |
| 2021/0128768 A1* | 5/2021 | Jackson .................. A61B 50/20 |
| 2021/0138517 A1 | 5/2021 | Kakar et al. |
| 2021/0186641 A1* | 6/2021 | Cummings ............. A61B 50/33 |
| 2021/0187141 A1 | 6/2021 | Crotti |
| 2021/0212796 A1* | 7/2021 | Crotti ........................ A61L 2/18 |
| 2021/0356051 A1* | 11/2021 | Gray-Dreizler ........ A61B 50/30 |
| 2022/0015862 A1* | 1/2022 | Rootes .................. B08B 7/0057 |
| 2022/0211458 A1* | 7/2022 | Jackson ................. A61B 50/33 |
| 2022/0304560 A1* | 9/2022 | Jackson ................. A61B 50/30 |
| 2022/0304762 A1* | 9/2022 | Jackson ............ A61B 1/00144 |
| 2022/0304764 A1* | 9/2022 | Jackson ..................... A61L 2/26 |
| 2022/0387651 A1 | 12/2022 | Kendrick |
| 2022/0392102 A1 | 12/2022 | Ohara et al. |
| 2023/0082582 A1* | 3/2023 | Jackson .................. A61B 50/13 |
| | | 206/363 |
| 2023/0285614 A1 | 9/2023 | Kotani et al. |
| 2023/0372567 A1* | 11/2023 | Hancock ................... A61L 2/14 |
| 2024/0238465 A1* | 7/2024 | Schroeder ................ A61L 2/24 |

FOREIGN PATENT DOCUMENTS

| | | |
|---|---|---|
| DE | 202016105248 | 12/2016 |
| EP | 0091792 B1 | 1/1988 |
| EP | 0830295 A1 | 3/1998 |
| EP | 2689706 A2 | 1/2014 |
| EP | 2900117 A1 | 8/2015 |
| JP | 2007054343 | 3/2007 |
| JP | 2009172228 | 8/2009 |
| JP | 2008054861 | 3/2020 |
| WO | 9607364 | 3/1996 |
| WO | 2011151641 | 12/2011 |
| WO | 2018024690 | 2/2018 |
| WO | 2018152400 A1 | 8/2018 |

OTHER PUBLICATIONS

International Preliminary Report on Patentability dated Dec. 30, 2021, of International PCT Application No. PCT/US/2020/036618 dated Jun. 8, 2020.

International Search Report and Written Opinion of the International Searching Authority Dated Sep. 9, 2020, of International PCT Application No. PCT/US2020/036618 filed Jun. 8, 2020.

Steelco ED200 Endoscope Drying/Storage Cabinet (Peacocks Medical Group) Jun. 20, 2018(Jun. 28, 2018) [retreived from the internet on Aug. 24, 2020 (Aug. 24, 2020) at https://web.archive.org/web/20180620034054/https://www.peacocks.net/medical-decontamination/endoscopy/endoscopy-drying-cabinetslsteelco-ed200.

International Preliminary Report on Patentability dated Dec. 30, 2021, of International PCT Application No. PCT/US/2020/036630 dated Jun. 8, 2020.

International Preliminary Report on Patentability dated Dec. 30, 2021, of International PCT Application No. PCT/US/2020/036635 dated Jun. 8, 2020.

International Preliminary Report on Patentability dated Sep. 9, 2022 of International PCT Application No. PCT/US/2021/018463 dated Feb. 18, 2021.

International Preliminary Report on Patentability dated Sep. 30, 2021, of International PCT Application No. PCT/US2020/019640, dated Feb. 25, 2020.

International Search Report and Written Opinion mailed May 6, 2021, in International Application No. PCT/US2021/018463 filed Feb. 18, 2021.

International Search Report and Written Opinion mailed Nov. 20, 2020, in International Application No. PCT/US2020/036635 filed Jun. 8, 2020.

International Search Report and Written Opinion of the International Searching Authority Dated Jun. 5, 2020, of International PCT Application No. PCT/US2020/019640 filed Feb. 25, 2020.

International Search Report and Written Opinion of the International Searching Authority Dated Sep. 3, 2020, of International PCT Application No. PCT/US2020/036630 filed Jun. 8, 2020.

\* cited by examiner

NO VALVE + FORCED FILTERED AIR PRESSURE

VALVE + FORCED FILTERED AIR PRESSURE

VENTED ENDOSCOPE TRAY COVERS, SYSTEMS AND METHODS

PRIORITY CLAIM

This application claims priority and benefit of U.S. Provisional application with Ser. No. 62/820,483, filed Mar. 19, 2019, entitled VENTED ENDOSCOPE TRAY COVERS, SYSTEMS AND METHODS, which is herein incorporated by reference in its entirety.

BACKGROUND

Endoscopes are well-known in the art and are commonly used for numerous medical procedures. After each use, an endoscope will undergo reprocessing by cleaning, disinfection and/or sterilization to reduce or prevent contaminants from settling onto the endoscope, as well as to prevent the spread of disease, viruses, bacteria, and illness.

After endoscope reprocessing, an endoscope is generally disposed within a tray and a cover can be secured to the perimeter of the tray. The tray can then be loaded into a cart. The endoscope is then transported from a reprocessing room, where it is dried, and then transported back to a procedure room.

To decrease contaminants from settling on the exterior of the endoscope or in the internal channels of an endoscope, it is desirable to not only have a cover temporarily secured to the tray but also to have forced filtered air circulating within channels of the endoscope. However, with current endoscope transport carts, forced filtered air cannot be provided during transportation because the carts and/or trays cannot be connected to a forced filtered air source.

Even if a cart and/or a tray were compatible so that it could be connected to a forced filtered air source, the cover temporarily secured to the tray would detach from the tray as the interior pressure of the forced filtered air within the tray would partially or completely remove the cover from the tray. The partially or completely uncovered reprocessed endoscope would no longer be protected from the outside environment as contaminants could enter into the tray where the reprocessed endoscope is stored, and the endoscope would become contaminated. This could be detrimental to a patient if the endoscope was used in an endoscopic procedure.

Thus, there is a need to develop new covers and methods that allow forced filtered air to be released from the tray, to reduce or inhibit the cover from being detached from the tray during transportation. There is also a need to develop a cover that reduces or inhibits contamination of the endoscope while forced filtered air is released from or into the tray.

SUMMARY

New devices, systems and methods are provided that allow forced filtered air to be released from the tray, to reduce or inhibit the cover from being detached from the tray during transportation. A one-way valve is attached to the cover, the one-way valve is configured to release air that escapes from the endoscope when filtered air is forced through the channels of an endoscope and released into a compartment of the tray.

In some embodiments, a cover for an endoscope storage tray is provided. The cover comprises a flexibly deformable material substantially impermeable to fluids. The flexibly deformable material is configured to be temporarily secured to the tray so as to cover an endoscope storage compartment of the tray. A one-way valve is attached to the cover that is configured to release air flowing from the endoscope storage compartment of the tray to the cover.

In some embodiments, an endoscope storage system is provided. The system comprises a cover for an endoscope storage tray. The cover comprising a flexibly deformable sheet material substantially impermeable to fluids. The flexibly deformable sheet material is configured to be temporarily secured to the tray so as to cover an endoscope storage compartment of the tray. A one-way valve is attached to the flexibly deformable sheet material and is configured to release air flowing from the endoscope storage compartment of the tray to the cover. A liner is configured to engage the endoscope storage compartment of the tray.

In some embodiments, an endoscope storage system is provided. The system comprises an endoscope storage tray having an endoscope storage compartment. A liner is configured to engage the endoscope storage compartment of the tray. A cover for the endoscope storage tray is provided comprising a flexibly deformable sheet material substantially impermeable to fluids. The flexibly deformable sheet material is configured to be temporarily secured to the tray so as to cover the endoscope storage compartment of the tray. A one-way valve is attached to the cover that is configured to release air flowing from the endoscope storage compartment of the tray to the cover.

In some embodiments, a method of making a cover for an endoscope storage tray is provided. The method comprises attaching a one-way valve to the cover, the cover comprising a flexibly deformable sheet material substantially impermeable to fluids, the flexibly deformable sheet material configured to be temporarily secured to the tray so as to cover an endoscope storage compartment of the tray, and the one-way valve configured to release air flowing from the endoscope storage compartment of the tray to the cover.

In some embodiments, a method of using a cover for an endoscope tray is provided. The method comprises temporarily securing a cover to an endoscope storage tray, the cover comprising a flexibly deformable sheet material substantially impermeable to fluids, the flexibly deformable sheet material configured to cover an endoscope storage compartment of the tray, the cover having a one-way valve attached thereto, the one-way valve configured to release air flowing from the endoscope storage compartment of the tray to the cover.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
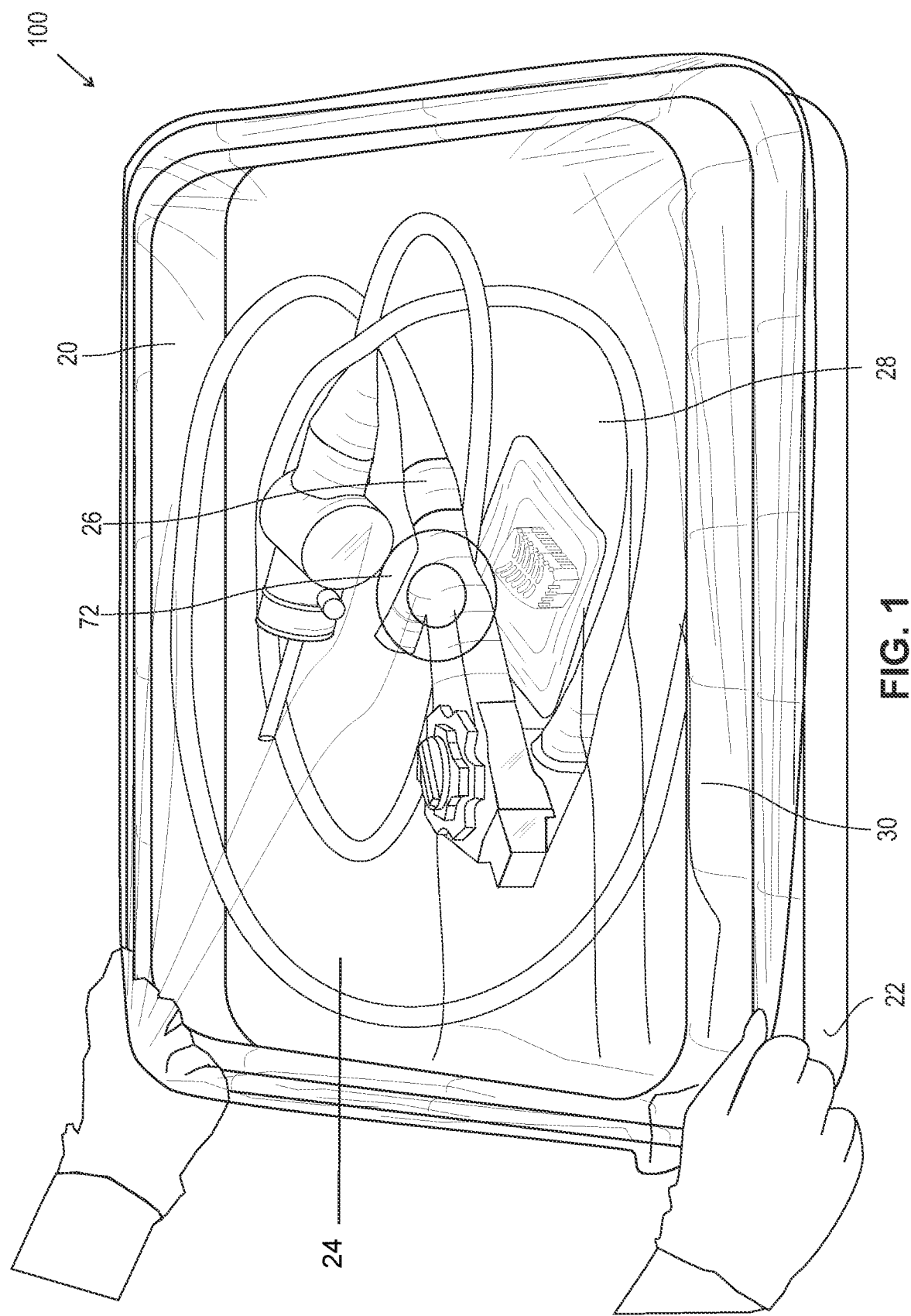
FIG. 1 illustrates a perspective view of a cover for an endoscope storage tray temporarily secured to the tray so as to cover an endoscope storage compartment of the tray. A one-way valve is attached to the cover that is configured to release air flowing from the endoscope storage compartment of the tray to the cover.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "outlet" includes one, two, three or more outlets.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

In some embodiments, a vented liner cover with a pressure valve is provided that allows air to escape from an interior of a tray. The vented liner cover maintains a pressure within the interior of the tray so that the cover does not detach from the tray. The cover comprises a one-way pressure valve that allows air to escape from the interior of the tray but prevents air from entering the interior of the tray, thereby preventing contaminants from entering into the tray. In some embodiments, the cover can be temporarily secured to a tray and the tray can be stored in a drying cabinet.

Cover

Referring to FIGS. 1-8, a cover 20 for a rigid endoscope storage tray 22 is provided. The cover is configured to facilitate release of air flowing from an endoscope storage compartment 24 of the tray to the cover when forced filtered air is supplied to working channels of a reprocessed endoscope 26 during tray transportation. In some embodiments, the cover is a disposable single use cover that may be sterile or unsterile. In some embodiments, the cover has some similar features to the cover found and described in U.S. Pat. No. 6,749,063, assigned to Cantel (UK) Limited. This patent is herein incorporated by reference.

The cover comprises a flexibly deformable material 28 that is substantially impermeable to fluids so as to protect the endoscope from external fluids that can contaminate the endoscope. The flexibly deformable material is configured to be temporarily secured to the tray so as to cover the endoscope storage compartment of the tray. Flexibly deformable is defined relative to the rigid tray, where the material is capable of being movable, bendable and/or moldable such that the material can be reshaped, stretched and/or manipulated. Substantially impermeable is defined as a material that is almost entirely impenetrable to fluids, preventing most fluids from passing through the material. In some embodiments, the cover material is substantially impermeable or is entirely impermeable to fluids and/or air.

Figure 2:
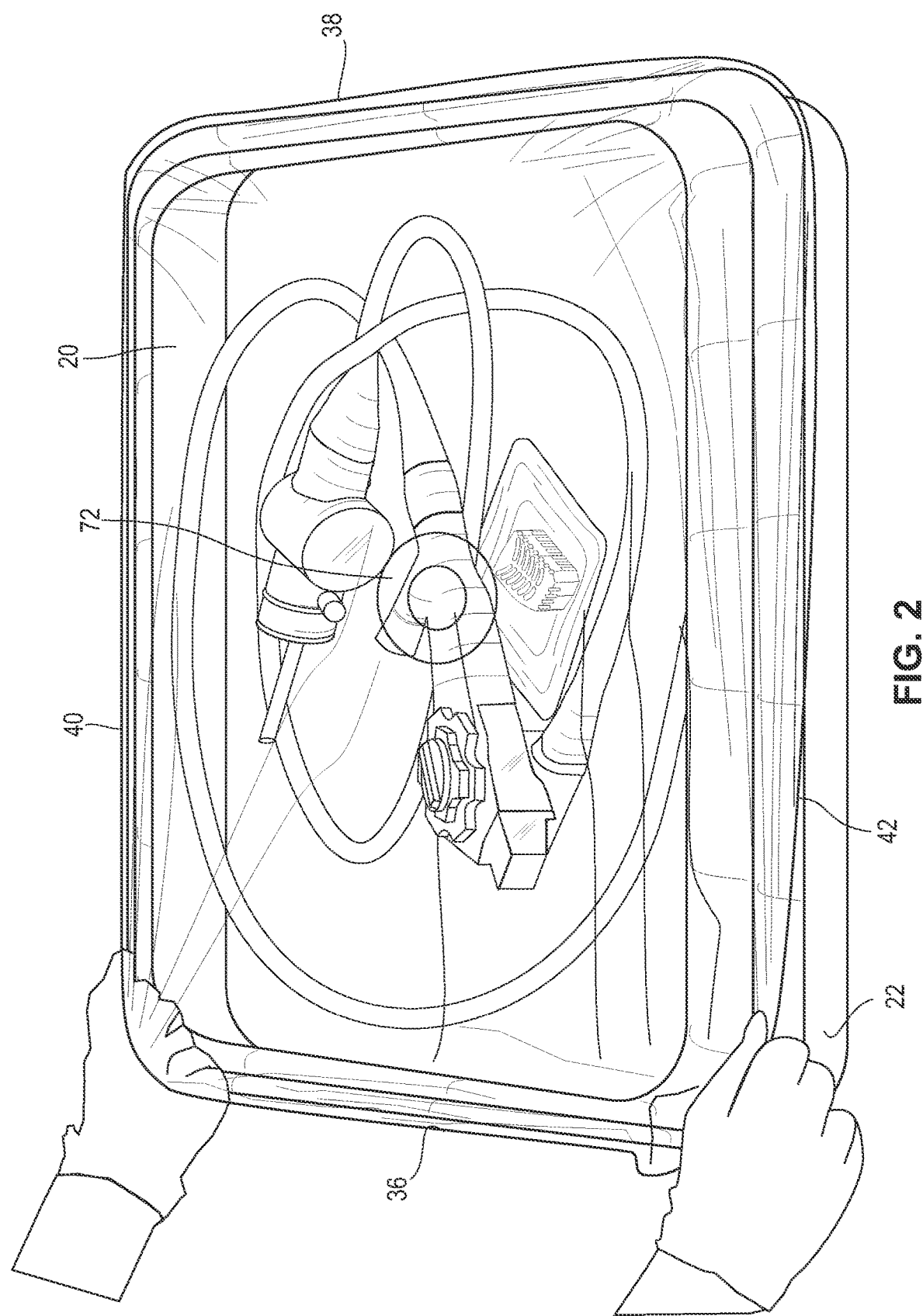
FIG. 2 illustrates a perspective view of the cover and tray, shown in FIG. 1.
Figure 3:
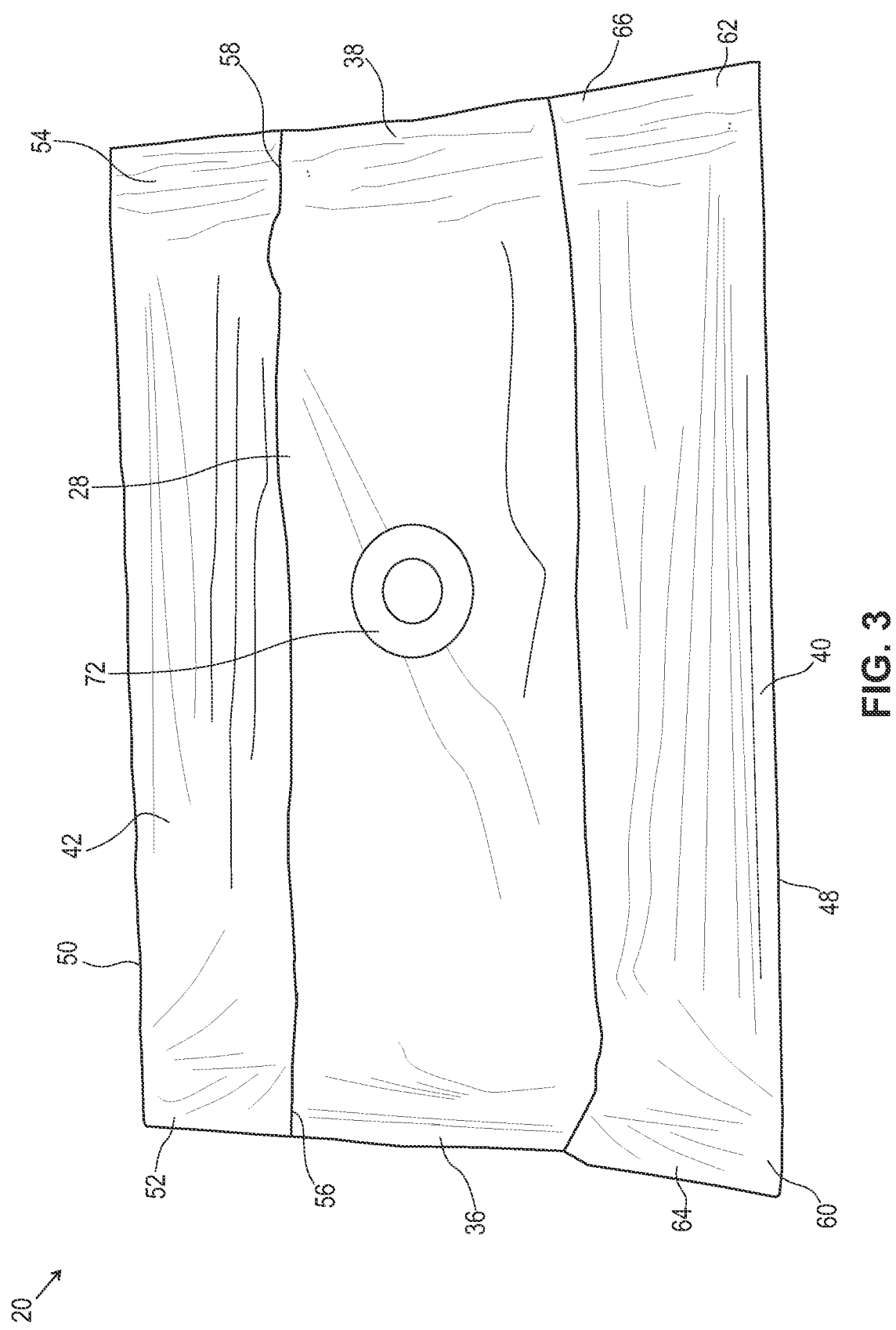
FIG. 3 illustrates a bottom view of the cover of FIG. 1 having a plurality of folds that are configured to be temporarily secured to the rim of the tray.

In some embodiments, the cover is in a sheet, wrap or bag configuration, as shown in FIGS. 1-5, and is configured to engage a rim 30, an exterior sidewall 32, a bottom 34, and/or a bottom exterior surface 35 of the tray. The flexibly deformable material extends between a first end 36 to an opposing second end 38, and includes a first edge 40 and an opposing second edge 42, as shown in FIGS. 2 and 3. The flexibly deformable material defines an inner surface 44 and an outer surface 46 disposed within the boundaries of the ends and edges. In some embodiments, the sheet, wrap or bag configuration can have a rectangular shape to correspond with the shape of the tray but other cover shapes are contemplated depending on tray shape. These shapes include oval, square, circular or the like.

In some embodiments, a plurality of folds, such as a first fold 48 and a second fold 50 are formed from a portion of the first edge and the second edge, respectively, as shown in FIG. 3. The plurality of folds are configured to be temporarily secured to the rim of the tray. The first fold extends between a proximal end 52 and a distal end 54. The proximal end of the first fold is attached to a portion of the first end at a junction point or a junction seam 56, and the distal end of the first fold is attached to a portion of the second end at a junction point or a junction seam 58 so as to form the first fold. The second fold extends between a proximal end 60 and a distal end 62. The proximal end of the second fold is attached to a portion of the first end at a junction point or a junction seam 64 and the distal end of the second fold is attached to a portion of the second end at a junction point or a junction seam 66 so as to form the second fold. In some embodiments, the plurality of folds can be secured to the rim of the tray via tension or an elastic band. In some embodiments, the plurality of folds can be secured to the rim of the tray by a removable adhesive.

Figure 4:
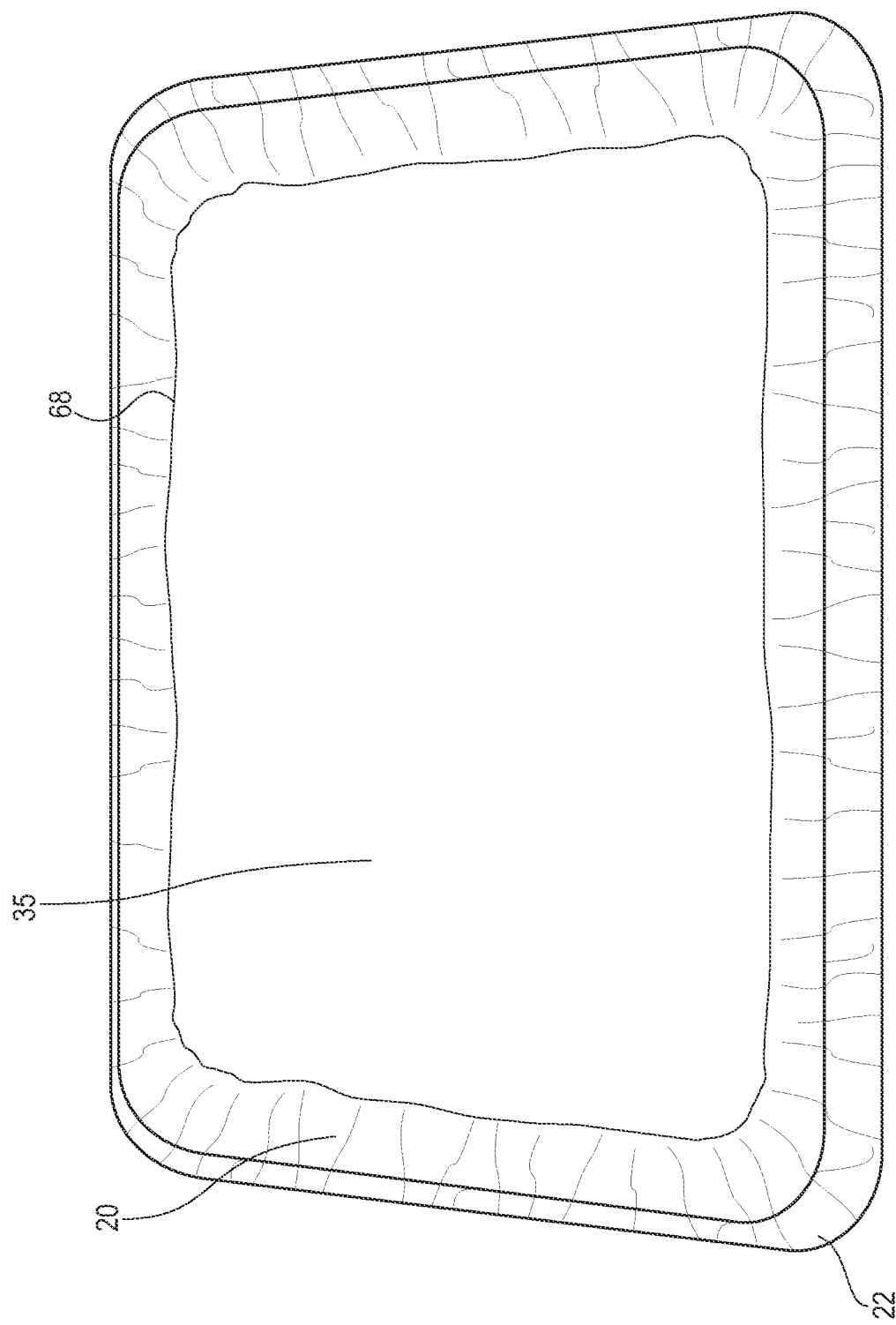
FIG. 4 illustrates a bottom view of the tray where a flexibly deformable material that the cover of FIG. 1 is made from comprises an elastic material that is configured to be temporarily secured to a bottom exterior surface of the tray.

In some embodiments, the flexibly deformable material is configured to be temporarily secured to the rim of the tray, and/or the bottom exterior surface of the tray. In some embodiments, the flexibly deformable material comprises an elastic material 68 configured to be temporarily secured to the bottom exterior surface of the tray, as shown in FIG. 4.

Figure 5:
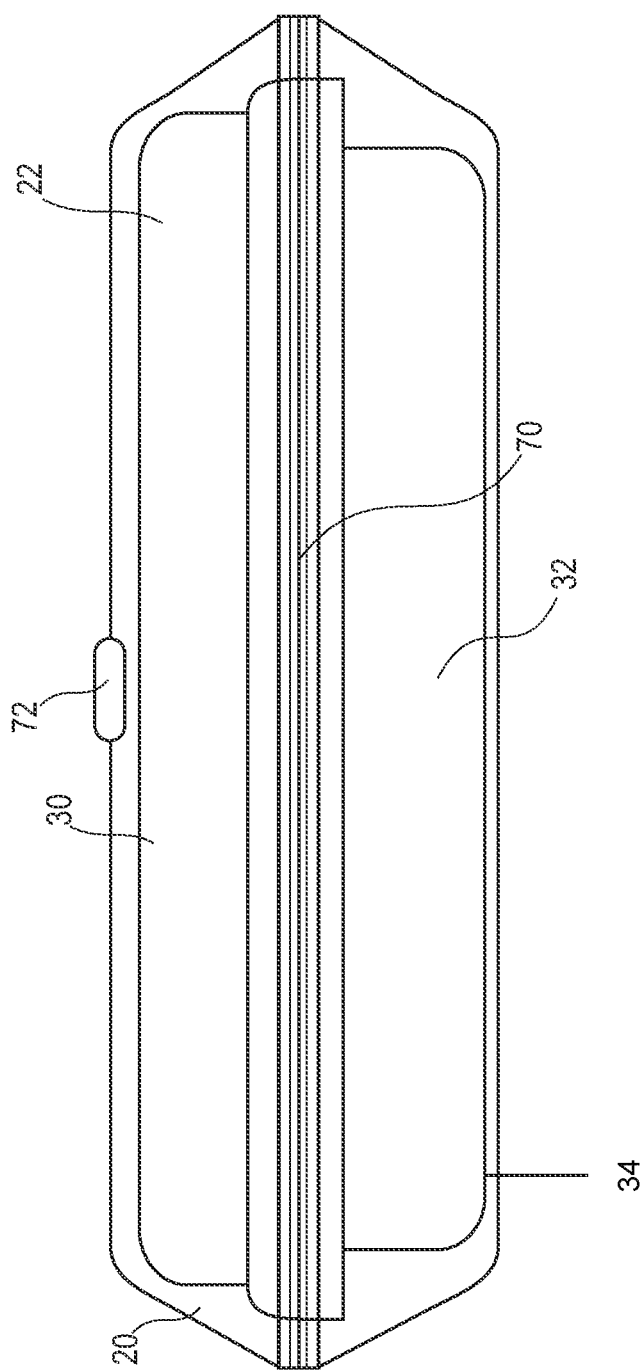
FIG. 5 illustrates a perspective view of an embodiment of the cover of FIG. 1 and the tray. In this embodiment, the cover is made from a flexibly deformable material that comprises a zip seal or an adhesive seal to enclose the tray.

In some embodiments, the flexibly deformable material is configured to entirely enclose the tray, as shown in FIG. 5. In some embodiments, the flexibly deformable material comprises a zip seal 70 or adhesive seal to enclose the tray. In some embodiments, the flexibly deformable material can alternatively be configured to partially enclose the tray.

Figure 6:
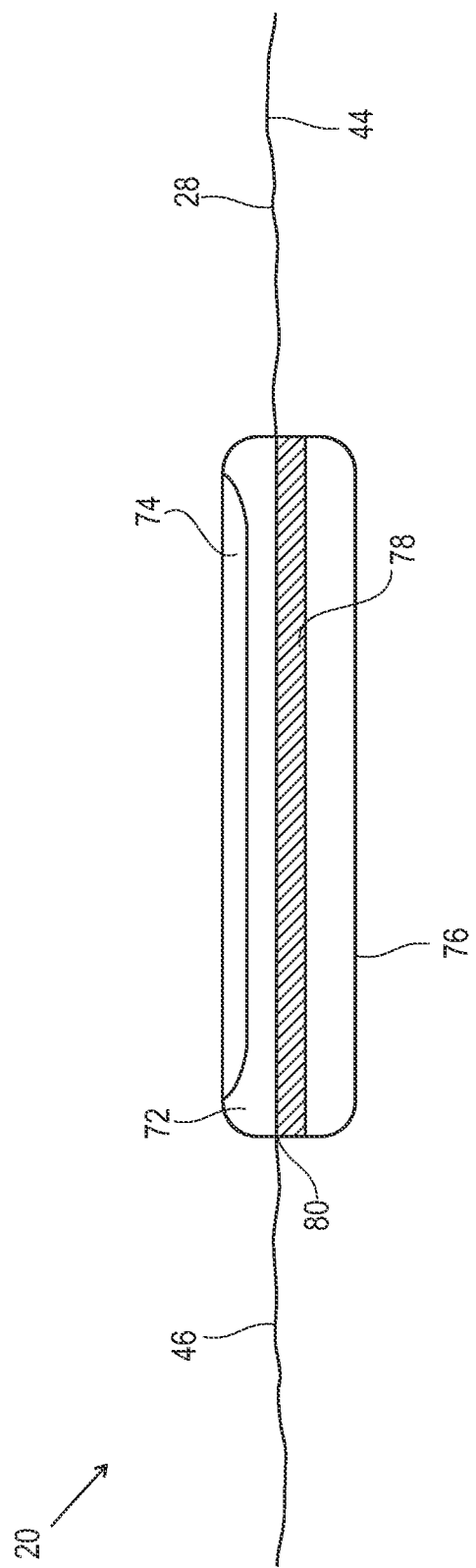
FIG. 6 illustrates a side view of the one-way valve of the cover of FIG. 1 and the tray. The one-way valve is a degassing valve and comprises an outlet configured to release air flowing from the endoscope storage compartment of the tray to the cover. The one-way valve is configured to fluidly couple the cover to the endoscope storage compartment of the tray.
Figure 6B:
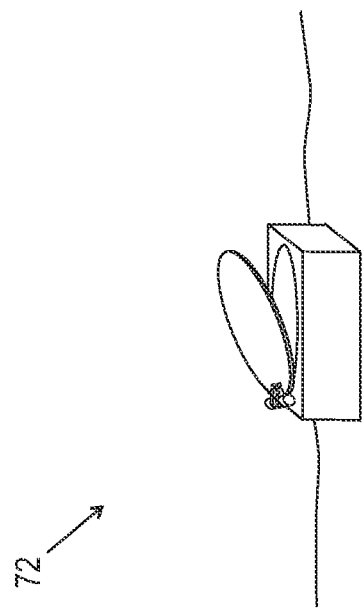
FIG. 6B illustrates a perspective view of an embodiment of the one-way valve of FIG. 6. In this embodiment, the one-way valve is a flap valve.
Figure 6A:
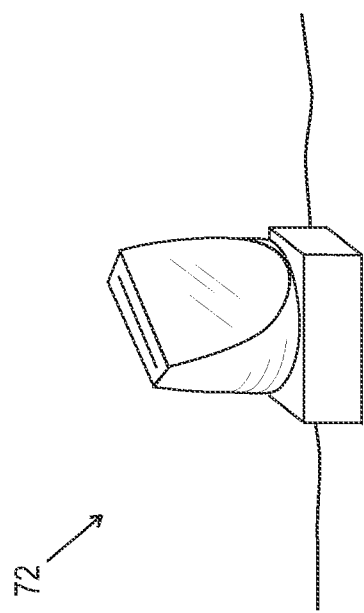
FIG. 6A illustrates a perspective view an embodiment of the one-way valve of FIG. 6. In this embodiment, the one-way valve is a duckbill valve.

A one-way valve 72 is attached to the cover. The one-way valve is configured to release air flowing from the endoscope storage compartment of the tray to the cover. The air can be forced filtered air flowing from an air source 116 (FIGS. 14-16) that uses a HEPA filter. In some embodiments, the one-way valve is configured to fluidly couple the cover to the endoscope storage compartment of the tray. The one-way valve can be a pressure valve or a degassing valve, as shown in FIG. 6, a duckbill valve, as shown in FIG. 6A or a flap valve, as shown in FIG. 6B. In some embodiments, the one-way valve can have similar features to the one-way valve found and described in U.S. Publication No. 2015/0259122, assigned to Cantel (UK) Limited. This publication is herein incorporated by reference.

The one-way valve is a controlling device for the passage of the forced filtered air in one direction and is controlled by the pressure applied to the one-way valve by the forced filtered air source. For example, the one-way valve will be closed when no forced filtered air is provided, however, when forced filtered air is provided, the pressure from the forced filtered air will force the one-way valve to open, thereby releasing the forced filtered air from the endoscope storage compartment and out of the cover. Therefore, it is to be understood that the one-way valve is a valve that allows the passage of air in one direction and that the one-way valve will open when the pressure inside the endoscope storage compartment is greater than the pressure outside of the cover. In some embodiments, the air flow from the forced filtered air will flow and open the one-way valve. This will prevent the cover from partially or completely uncovering the tray and therefore prevent contaminants from entering in or on the reprocessed endoscope.

The one-way valve comprises an outlet 74 configured to release air flowing from the endoscope storage compartment of the tray to the cover, as shown in FIG. 6, an inlet 76 to allow air flowing from the endoscope storage compartment to enter the one-way valve, and a seal 78 that allows only air to enter the inlet for release out of the outlet. The seal is disposed between the inlet and the outlet and is a movable barrier configured to reduce or prevent contaminants from entering into the endoscope storage compartment of the tray.

The cover can include an opening 80 that is configured to receive the one-way valve. The opening can be larger, smaller or the same size as the one-way valve. In some embodiments, the opening and the one-way valve are circular shaped. The inlet or outlet can further or alternatively engage the inner surface or the outer surface of the flexibly deformable material. The one-way valve can be positioned within or on the cover in a few ways. For example, the one-way valve can be centrally attached to the flexibly deformable material or can be attached to the flexibly deformable material adjacent to one of the edges of the flexibly deformable material. In some embodiments, the one-way valve is attached to the cover by an adhesive, tape and/or Velcro®.

Figure 7:
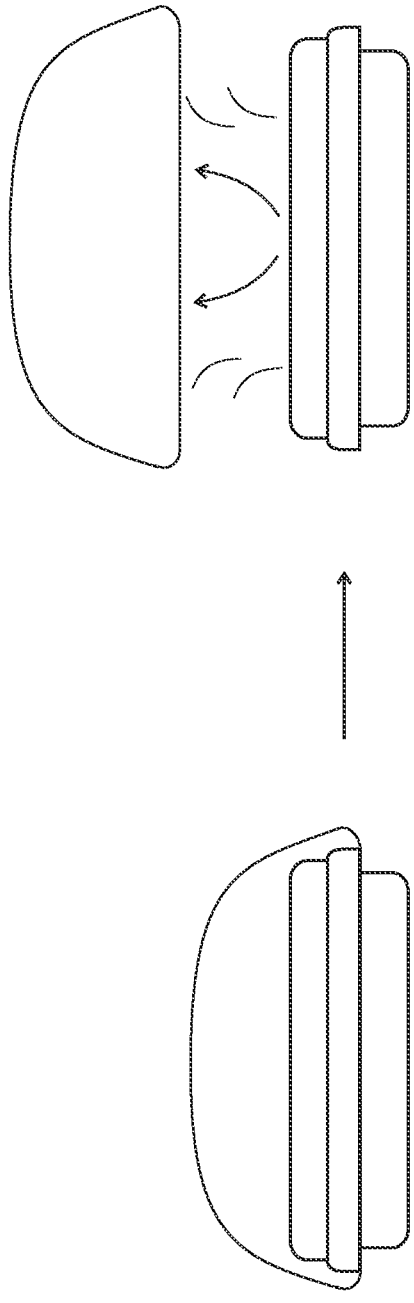
FIG. 7 illustrates a side view of a tray secured with a cover that does not include a one-way valve. The cover is shown detaching from the tray since there is no way for the forced filtered air to be released from the endoscope storage compartment of the tray. The tray is shown completely uncovered.
Figure 8:
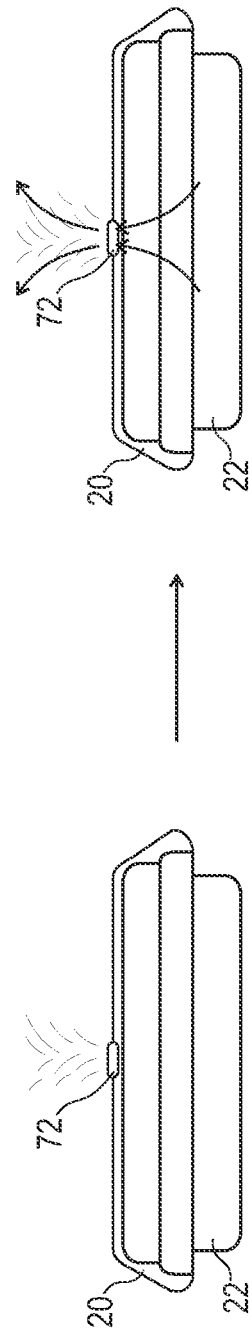
FIG. 8 is a side view of the tray of FIG. 1 secured with the cover of FIG. 1. The cover is shown not detaching from the tray since the one-way valve allows for the forced filtered air to be released from the endoscope storage compartment of the tray. This occurs when a predetermined amount of pressure is reached. The one-way valve opens in one direction to release the air pressure when it is above a predetermined pressure.

As shown in FIGS. 7 and 8, when a cover does not include a one-way valve (FIG. 7), forced filtered air entering into the endoscope storage compartment of the tray would create an interior pressure that would detach the cover from the tray since the forced filtered would have no way of escaping out of the tray. Thus, the endoscope would no longer be protected from the outside environment and could be subjected to environmental contaminates. When a cover does include a one-way valve, as described herein (FIG. 8), forced filtered air will be released from the endoscope storage compartment of the tray through the one-way valve, preventing the cover from detaching from the tray. In this way, the reprocessed endoscope maintains disinfection and is not subjected to external environmental factors.

In some embodiments, a pressure differential will exist between the endoscope storage compartment when forced filtered air is present and the outside environment surrounding the cover and tray. In some embodiments, the pressure differential can be from about 0.5 to about 10 pounds per square inch (PSI). In some embodiments, the pressure differential can be from about 0.5, 0.6, 0.7, 0.8, 0.9, 1, 2, 3, 4, 5, 6, 7, 8, 9 to about 10 pounds per square inch (PSI). In order to decrease the pressure differential, the one-way valve releases the forced filtered air from the inside of the endoscope storage compartment and out of the cover.

In some embodiments, the cover can be manufactured at a certain sheet thickness. In some embodiments, the sheet thickness of the cover can be from about 100 micrometers (μm) to about 4 millimeters (mm). In some embodiments, the sheet thickness of the cover can be from about 100 μm, 200 μm, 300 μm, 400 μm, 500 μm, 600 μm, 700 μm, 800 μm, 900 μm, 1 mm, 2 mm, 3 mm to about 4 mm.

In some embodiments, the cover can have certain dimensions. In some embodiments, the dimensions of the cover are from about 18 inches to about 30 inches in length and from about 14 to about 24 inches in width. In some embodiments, the dimensions of the cover are from about 18, 19, 20, 21, 22, 23, 24, 25, 26, 27, 28, 29 to about 30 inches in length and from about 14, 15, 16, 17, 18, 19, 20, 21, 22, 23 to about 24 inches in width.

In some embodiments, the flexibly deformable sheet material is made from a high-density polythene (HDP). In some embodiments, the flexibly deformable sheet material can be made from other materials such as, for example, high-density polyethylene (HDPE), low-density polyethylene (LDPE), and/or linear low-density polyethylene (LLDPE).

The cover can be manufactured in different colors such as in a green or a clear color to indicate that the endoscope is clean and ready for use. Alternative colors can be selected such as blue, pink, yellow, red, orange, brown or black. In some embodiments, the cover can be reversible and a different color can be used on the inner surface than on the outer surface of the cover.

In some embodiments, the components of the one-way valve can be made from a material such as, for example, a polymeric material. The polymeric material can be thermoplastic and/or is a polycarbonate. For example, the one-way valve can be fabricated from materials such as machined or injection molded thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers, polymeric rubbers, polyolefin rubbers, semi-rigid and rigid materials, elastomers, rubbers, thermoplastic elastomers, thermoset elastomers, elastomeric composites, polyphenylene, polychloropene, polyamide, polyetherimide, polyethylene, epoxy, partially resorbable materials, totally resorbable materials, polyglycolide, polytyrosine carbonate, polycaprolactone, silicone based rubber, liquid silicone rubber, High Consistency Rubber, silicon, TPE, Polypropylene, Polycarbonate, ABS or any combination thereof.

In some embodiments, the one-way valve can be a certain diameter ranging from about 0.5 centimeters (cm) to about 6 cm. In some embodiments, the one-way valve can have a diameter of 0.5, 0.6, 0.7, 0.8, 0.9, 1, 1.5, 2, 2.5, 3, 3.5, 4, 4.5, 5, 5.5 to about 6 cm.

The components of the one-way valve, individually or collectively, may also be fabricated from a heterogeneous material such as a combination of two or more of the above-described materials. The one-way valve as described herein may be constructed of a suitable biocompatible material to impart various desirable characteristics, such as flexibility, and resilience.

In some embodiments, components of the one-way valve can also be made from a suitable material such as for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), plastic (e.g., polycarbonates), ABS, MABS, or the like or combinations thereof.

In some embodiments, the seal may be formed from a suitable material, such as metal, polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), rubber, plastic, or the like or combinations thereof or any of the materials as described herein.

In some embodiments, contaminants can include, but are not limited to, biological contaminants such as microorganisms including bacteria, viruses, yeasts, molds and parasites; air borne contaminants such as airborne microbes; and/or chemical contaminants. In some embodiments, bacterial can include, but is not limited to *Escherichia coli, Klebsiella* species, *Enterobacter* species, enterococci, *Pseudomonas aeruginosa* and *Salmonella* species.

Storage System

Referring to FIGS. 9-18, an endoscope storage system 100 is provided. The system is configured to facilitate release of air flowing from the endoscope storage compartment of the tray to the cover when forced filtered air is supplied to working channels of a reprocessed endoscope or to the reprocessed endoscope during tray transportation. The reprocessed endoscopes can be obtained from automated endoscope reprocessors obtained from, for example, Medivators Inc., Mn USA. In some embodiments, the system is also configured for storing an endoscope after the endoscope has been decontaminated. The system comprises cover 20 including one-way valve 72, as described above and a liner 102, as shown in FIG. 9. In some embodiments, the liner is configured to engage the endoscope storage compartment of the tray. The liner can contact the endoscope storage compartment of the tray and an endoscope. In some embodiments, the liner is similar to the liner found and described in U.S. Pat. No. 6,749,063, assigned to Cantel (UK) Limited. This patent herein is incorporated by reference.

Figure 9:
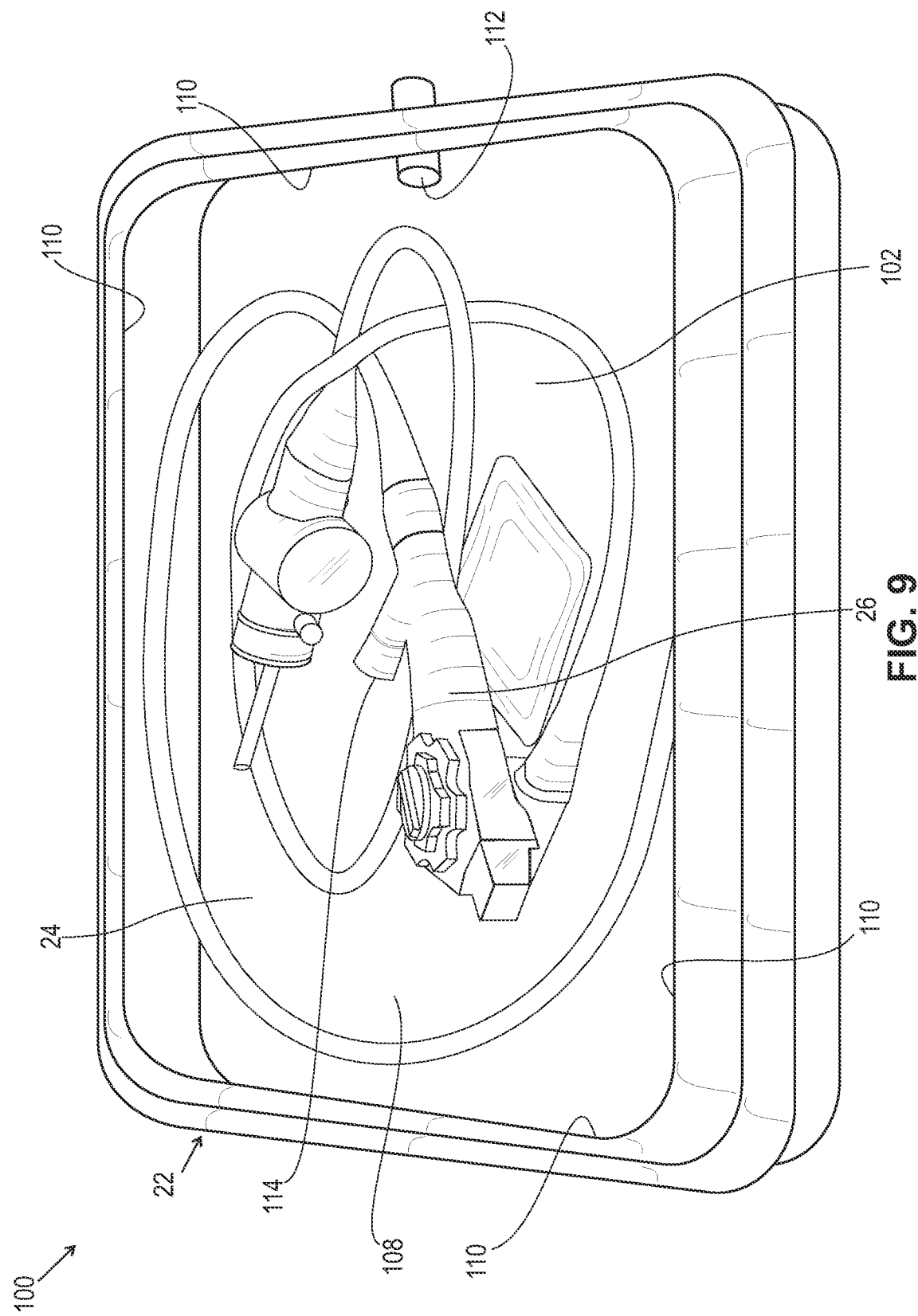
FIG. 9 illustrates a perspective view of an endoscope storage tray optionally comprising an outlet configured to engage working channels of an endoscope. A liner is shown contacting the storage compartment of the tray and an endoscope is disposed with the storage compartment.
Figure 10:
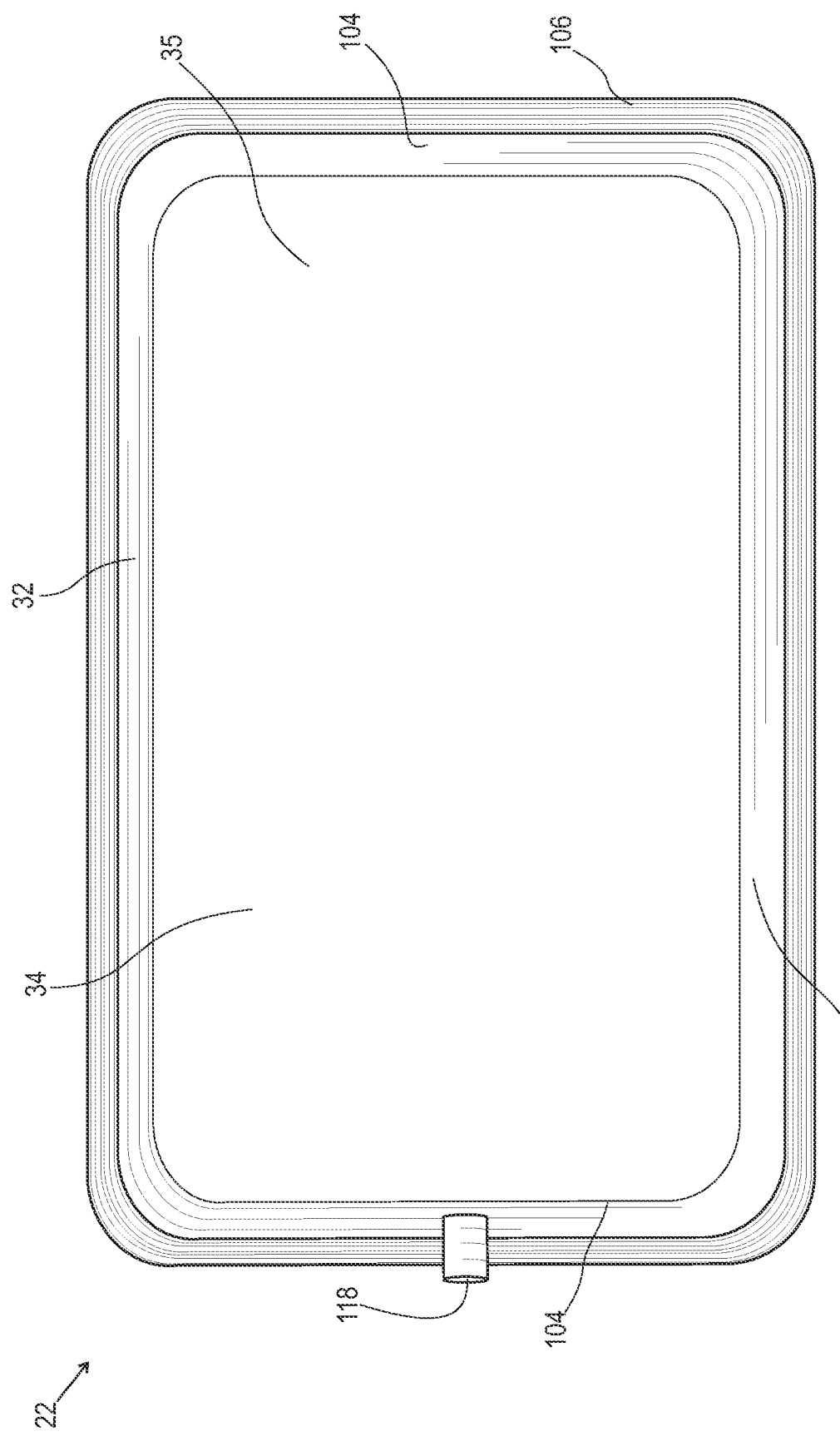
FIG. 10 illustrates a bottom view of the tray of FIG. 9.
Figure 11:
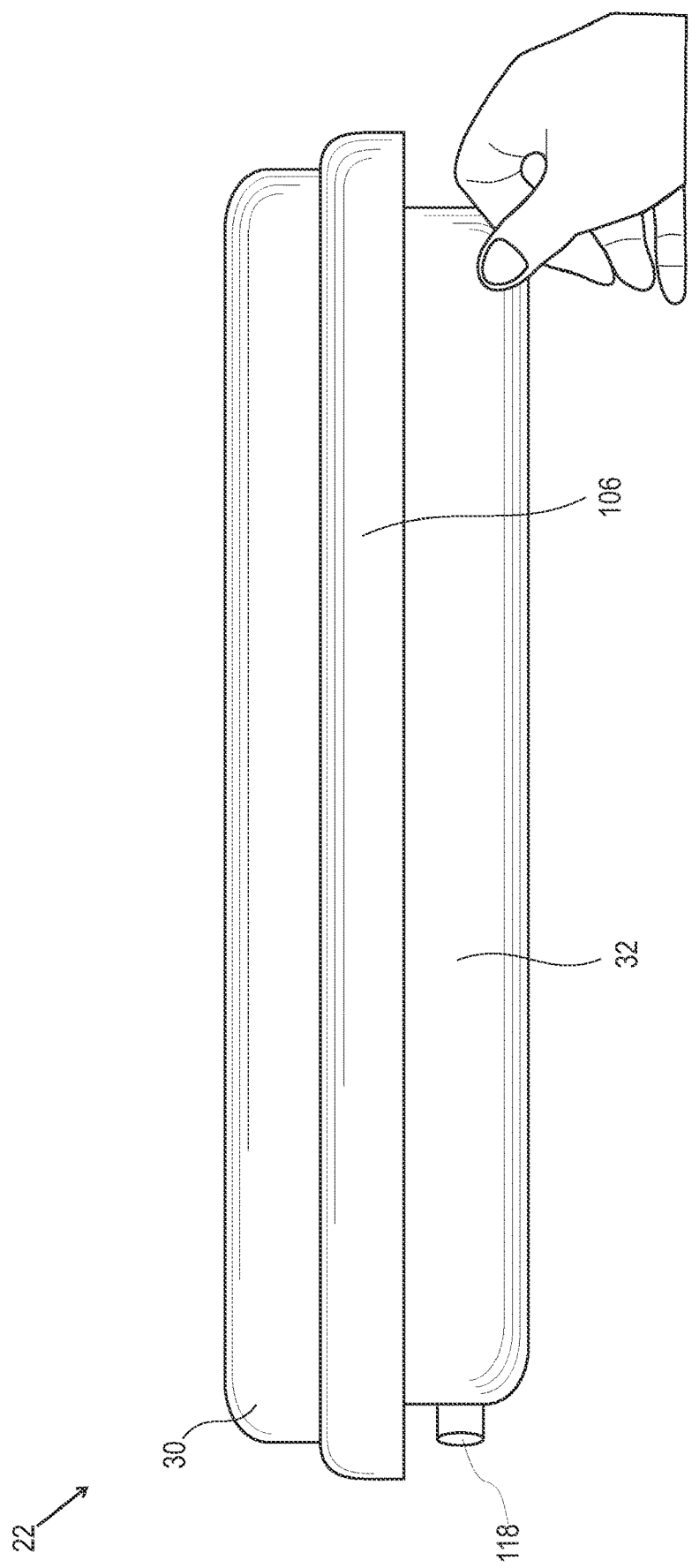
FIG. 11 illustrates a side view of the tray of FIG. 9.
Figure 17:
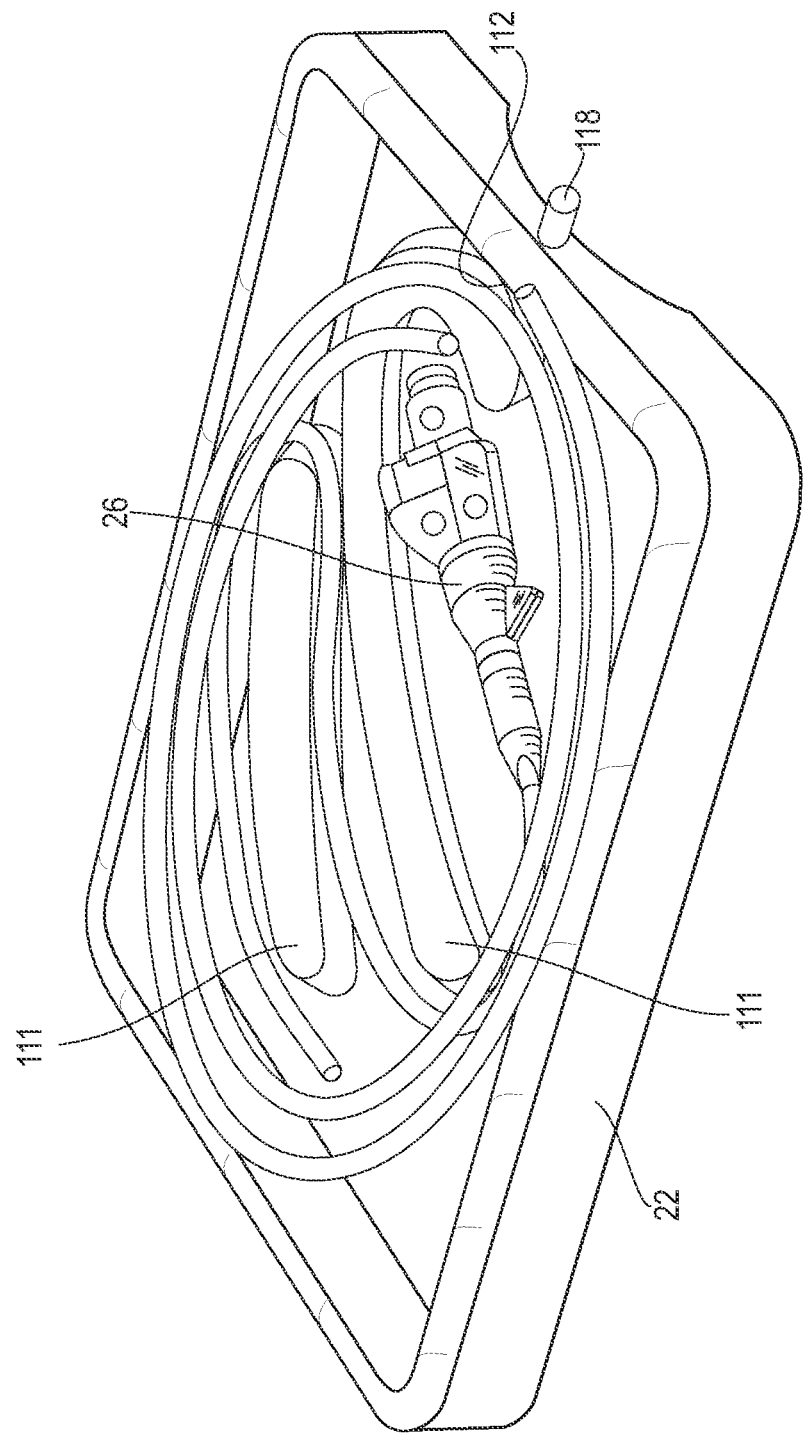
FIG. 17 illustrates a perspective view of an embodiment of a traying having upstanding elements to store an endoscope. The tray can have an inlet to receive forced filtered air and an outlet to direct the air to the endoscope.

In some embodiments, the system further includes endoscope storage tray 22, as described above. In some embodiments, the tray is a rigid, reusable tray. In some embodiments, the tray is similar to the tray described in U.S. Pat. No. 6,749,063, assigned to Cantel (UK) Limited. This parent herein is incorporated by reference. The tray includes exterior sidewall 32, opposing end walls 104, and rim 30 that is curled over to form a lip portion 106. Bottom 34 includes exterior bottom surface 35 and the bottom contacts the exterior side wall and the end walls. The endoscope storage compartment 24 of the tray comprises a planar base 108 and surrounding walls 110 upstanding therefrom, as shown in FIG. 9. In some embodiments, the entire tray base can be planar, while other portions of the tray can be planar, while other portions of the tray can be non-planar or arched, defining upstanding elements 111, as shown in FIG. 17.

Figure 14:
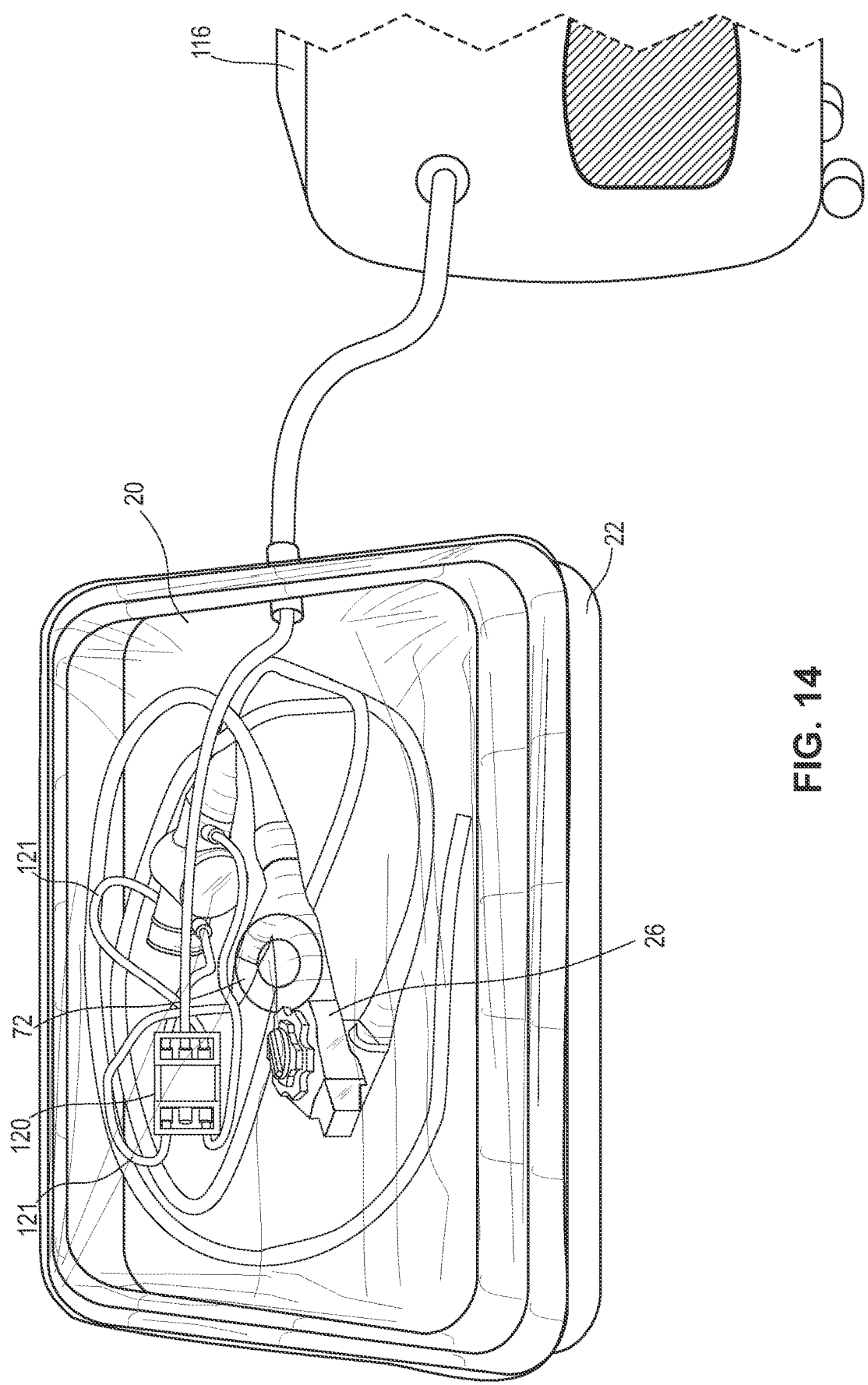
FIG. 14 illustrates a perspective view of the tray of FIG. 9 optionally comprising an outlet, an endoscope disposed within the tray, and an outlet member configured to engage with the outlet of the tray and working channels of the endoscope to receive forced filtered air. A forced filtered air source, using a high efficiency particulate air (HEPA) filter is attached to the outlet member.
Figure 16:
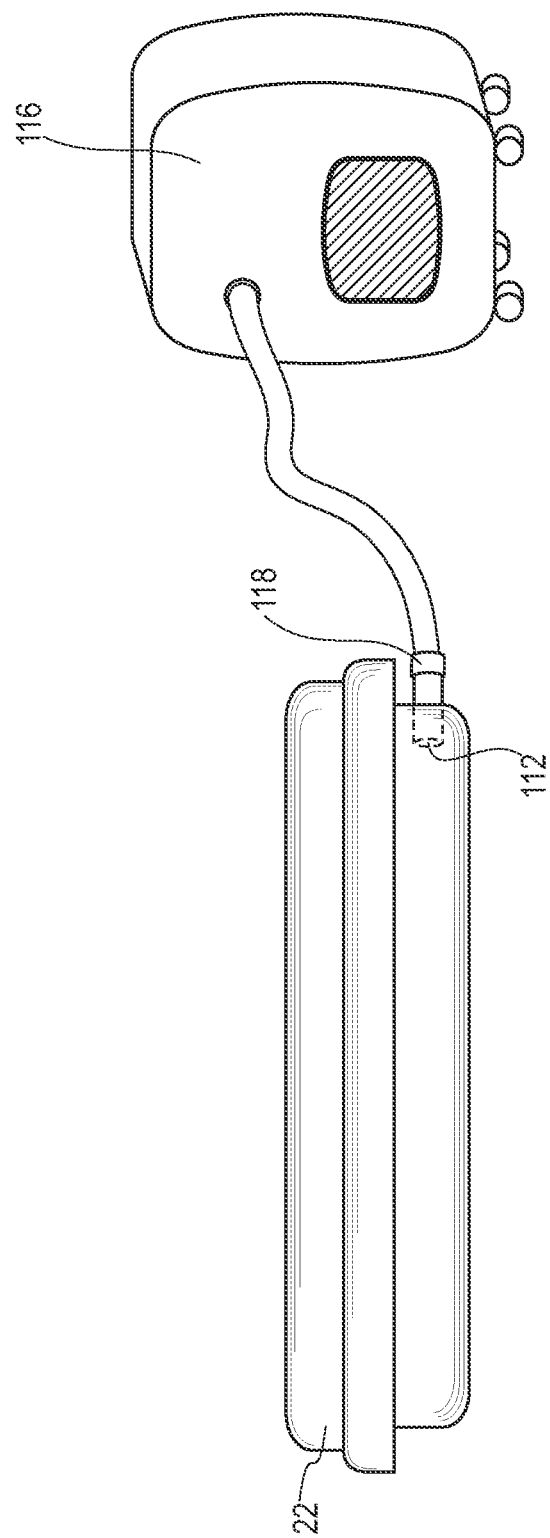
FIG. 16 illustrates a perspective view of the tray of FIG. 9 optionally comprising an outlet configured to engage working channels of the endoscope to receive forced filtered air flowing from a forced filtered air source using a HEPA filter.

In some embodiments, the tray comprises an outlet 112, as shown in FIGS. 9, 14 and 16 configured to engage a working channel 114 of the endoscope to receive forced filtered air. The forced filtered air can be supplied by an air source 116 that utilizes a HEPA filter that is attached to an inlet 118 defined by the tray. In some embodiments, the HEPA filter can be made from thin fibers of glass and can contain an amount of an activated carbon-based material. The forced filtered air can be either released into the endoscope storage compartment of the tray by the outlet or the forced filtered air can be released into tubes that are attached to the outlet. In some embodiments, the outlet and/or inlet can be formed from the side walls, end walls and/or the bottom of the tray.

Figure 12:
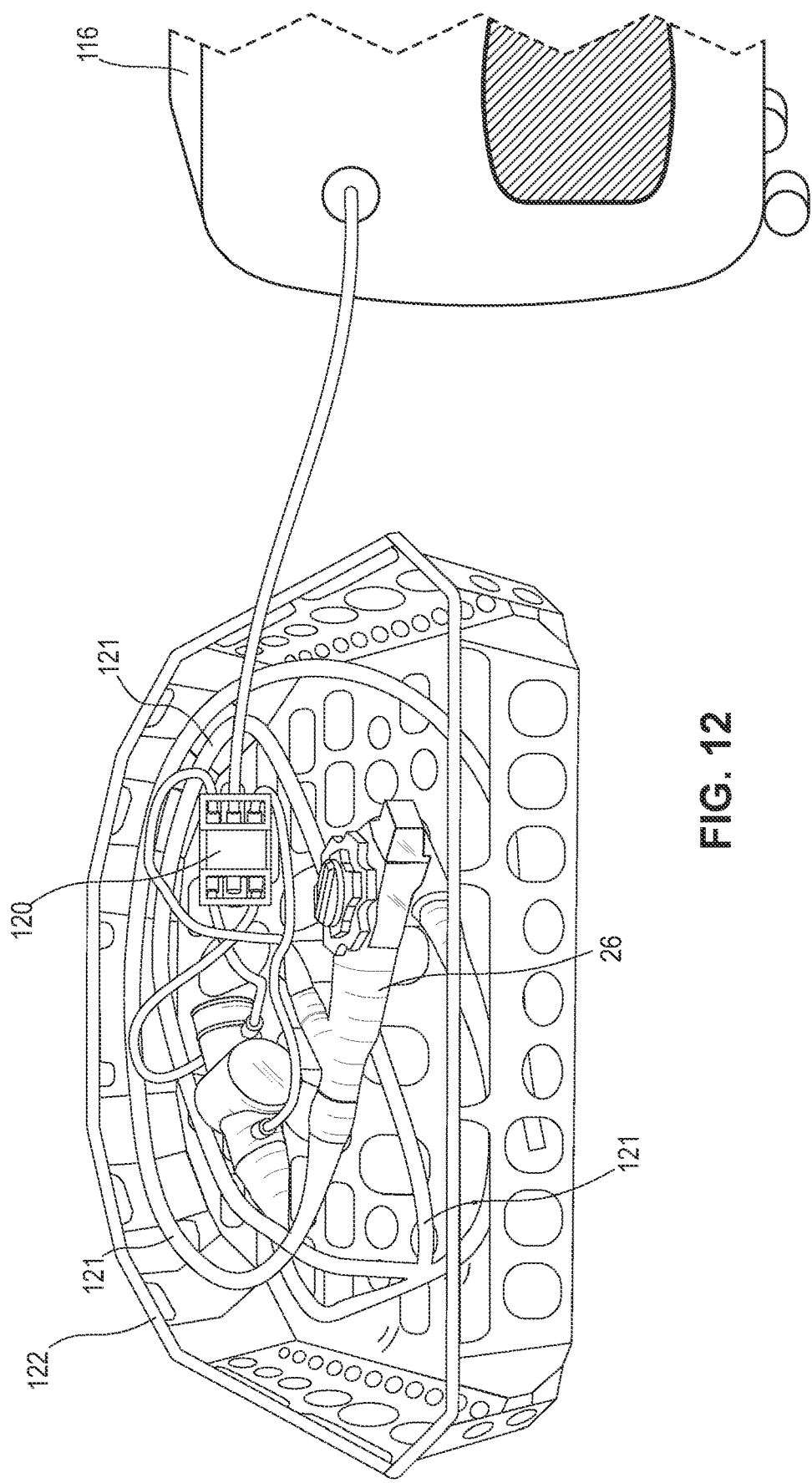
FIG. 12 illustrates a perspective view of a basket, an endoscope disposed within the basket, and an outlet member configured to engage working channels of the endoscope to receive forced filtered air. A forced filtered air source, using a high efficiency particulate air (HEPA) filter is attached to the outlet member.
Figure 13:
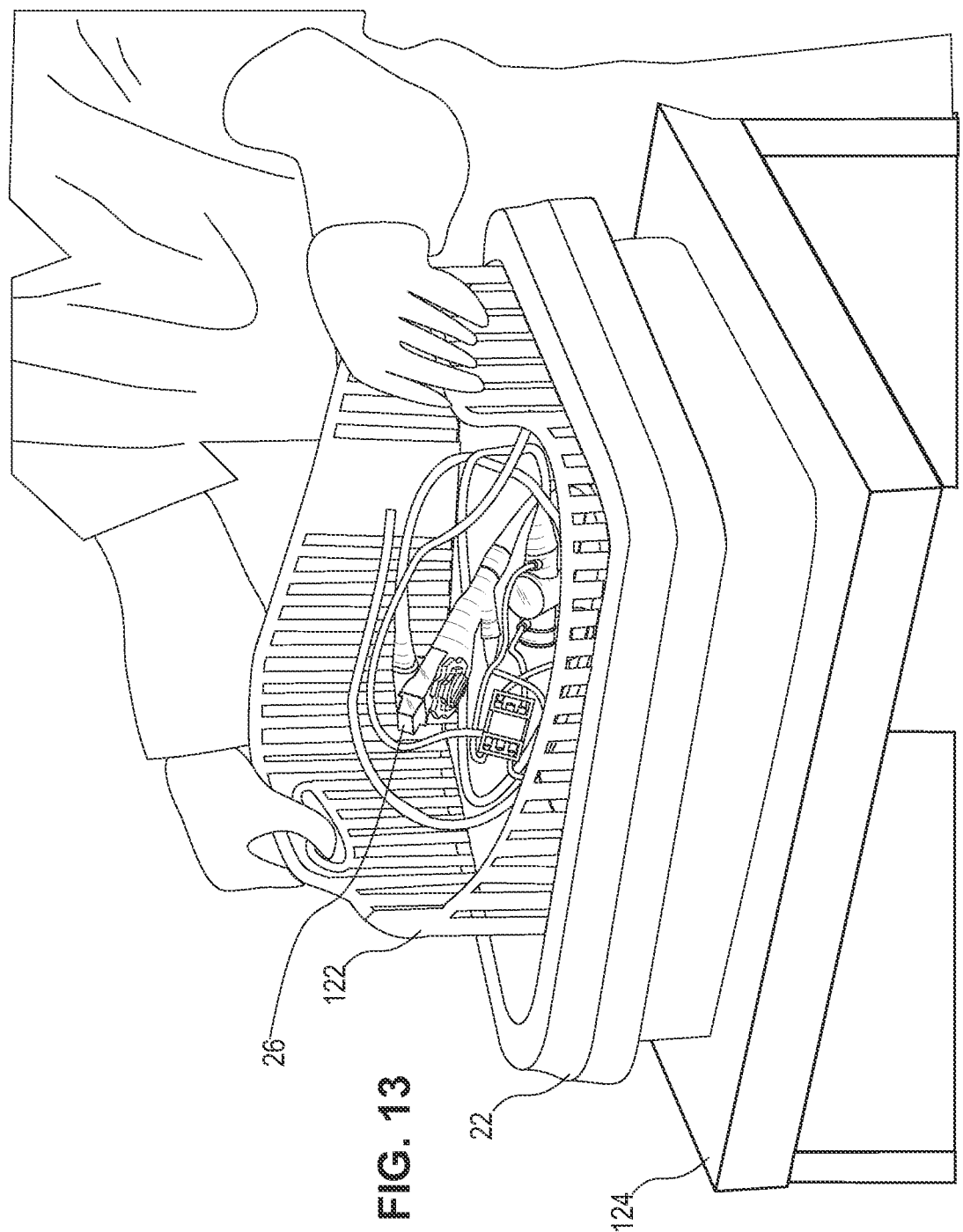
FIG. 13 illustrates a perspective view of the basket of FIG. 12 being disposed within the endoscope storage compartment of the tray of FIG. 9 by a user.

In some embodiments, an outlet member, or a hook up block 120 is alternatively provided that is configured to engage one or more working channels of the endoscope to receive forced filtered air. A hook up block can be a member having one or more conduits and/or tubes that allow air/gas and/or fluids to travel to the desired location. The outlet member can include one or a plurality of tubes 121 configured to engage one or more working channels. The outlet member can be disposed directly into the endoscope storage compartment, as shown in FIG. 14 or it can be disposed within a basket 122 that is disposed within the endoscope storage compartment, as shown in FIG. 12. Forced filtered air can then be received by the outlet member by the air source that uses a HEPA filter. In some embodiments, the basket provides touch-free endoscope handling to reduce cross-contamination while protecting the endoscope during transport to reduce endoscope damage.

Figure 15:
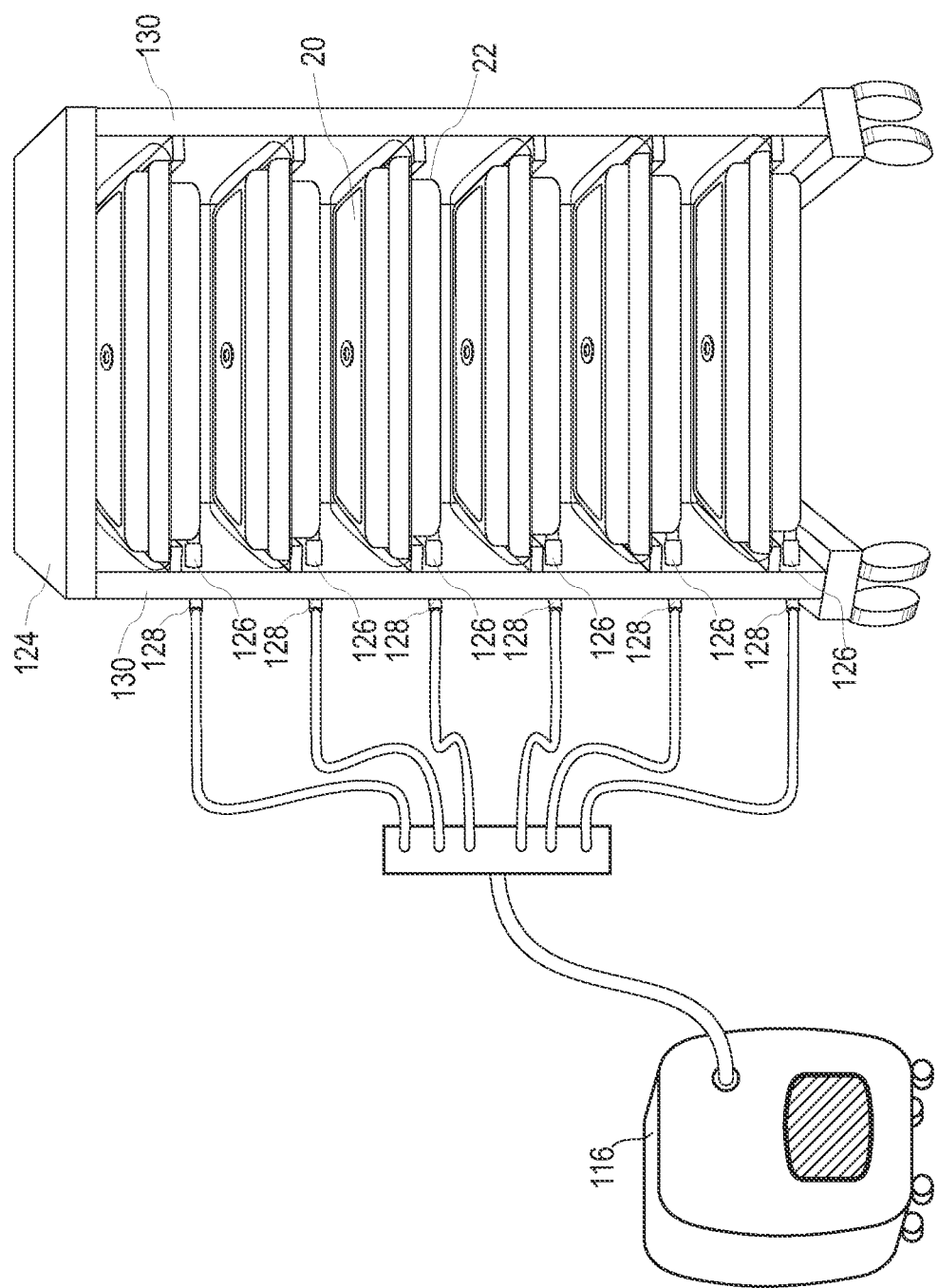
FIG. 15 illustrates a perspective view of a cart configured to store a plurality of endoscope storage trays and a plurality of outlets configured to engage working channels of the endoscopes to receive forced filtered air. A forced filtered air source using a HEPA filter is attached to the outlet.

In some embodiments, the system further comprises a cart 124 configured to store a plurality of endoscope storage trays, as shown in FIG. 15. The cart can comprise an outlet 126 configured to engage a working channel of the endoscope to receive forced filtered air. The forced filtered air can then be supplied by the air source that uses a HEPA filter which is attached to an inlet 128 defined by the cart. The outlet and the inlet can be defined from walls 130 of the cart.

In some embodiments, the cart comprises one or more inlets and outlets. In some embodiments, the cart comprises 1, 2, 3, 4, 5, 6, 7, 8, 9 or 10 inlets and outlets. In some embodiments, only 1 inlet and 1 outlet are defined by the cart and the forced filtered air is supplied to all of the plurality of endoscope storage trays by the 1 outlet and the 1 inlet. Alternatively, a plurality of outlets and inlets are defined by the cart such that each outlet and inlet supply forced filtered air to each individual endoscope storage tray, as shown in FIG. 15. In some embodiments, the cart and/or the tray comprises an outlet.

In some embodiments, the cart comprises the outlet member or hookup block, 120, that is configured to engage a working channel of the endoscope to receive forced filtered air. The outlet member will be attached to the filtered air source, similar to what is shown in FIG. 12.

Figure 18:
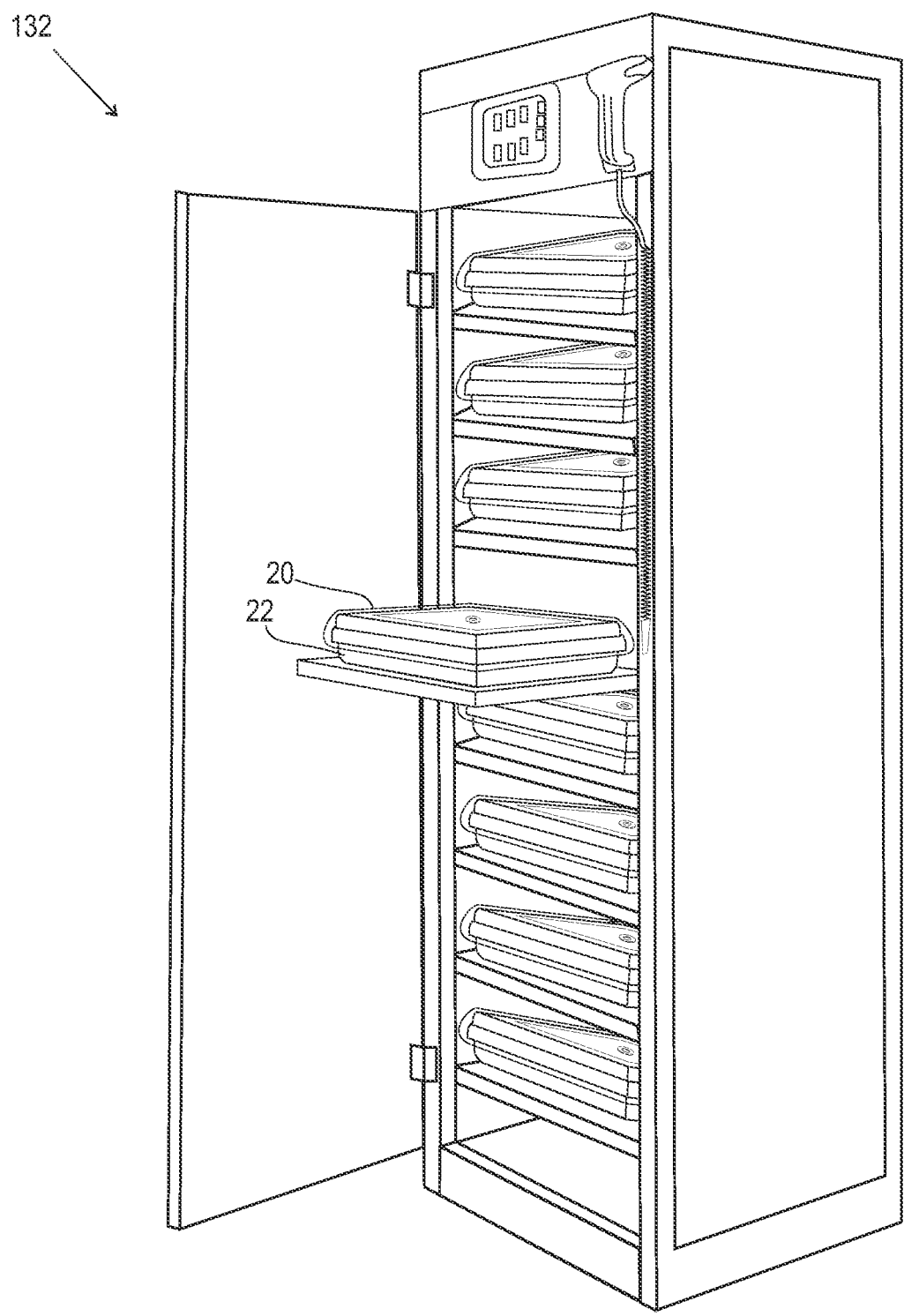
FIG. 18 illustrates a perspective view of a drying cabinet configured to store a plurality of endoscope storage trays.

In some embodiments, the system further comprises a drying cabinet 132 to store a plurality of endoscope storage trays, as shown in FIG. 18. The drying cabinet is similar to the drying cabinet found and described in International Publication No. WO2018/024690A1, assigned to Cantel (UK) Limited. The entire disclosure is herein incorporated by reference. In some embodiments, one or more endoscopes can be disposed within either an endoscope storage tray, within a basket, and/or within a basket that is disposed with an endoscope storage tray. While in the drying cabinet, the outlet member or hookup block 120 can be configured to engage a working channel of the endoscope to receive forced filtered air by the air source.

Methods and Kits

A method of making a cover for an endoscope storage tray is provided. The method comprises attaching a one-way valve to the cover, the cover comprising a flexibly deformable sheet material substantially impermeable to fluids, the flexibly deformable sheet material configured to be temporarily secured to the tray so as to cover an endoscope storage compartment of the tray, and the one-way valve configured to release air flowing from the endoscope storage compartment of the tray to the cover.

In some embodiments, the one-way valve is a pressure valve and comprises an inlet, an outlet and a seal. In some embodiments, the one-way valve is attached to the cover by adhesive, tape or Velcro®. It is to be understood that the cover is cover 20, as described above.

In some embodiments, a method of using a cover for an endoscope tray is provided. The method comprises temporarily securing a cover to an endoscope storage tray, the cover comprising a flexibly deformable sheet material substantially impermeable to fluids, the flexibly deformable sheet material configured to cover an endoscope storage compartment of the tray, the cover having a one-way valve attached thereto, the one-way valve configured to release air flowing from the endoscope storage compartment of the tray to the cover.

In some embodiments, the flexibly deformable sheet material comprises a plurality of folds configured to be temporarily secured to a rim of the tray. In some embodiments, the flexibly deformable sheet material is configured to be temporarily secured to a bottom exterior surface of the tray. In some embodiments, the flexibly deformable sheet material comprises an elastic material configured to be temporarily secured to a bottom exterior surface of the tray.

In some embodiments, the flexibly deformable sheet material is configured to entirely enclose the tray. In some embodiments, the flexibly deformable sheet material is configured to partially enclose the tray. In some embodiments, the endoscope storage tray is a semi-rigid and reusable tray. It is to be understood that the cover is cover 20, as described above.

It will be recognized by one of ordinary skill in the art that numerous steps in the manufacturing process may be optional or may be performed in a different sequence than specifically shown. The scope of the manufacturing process is not limited to the particular sequence and steps discussed herein, except as expressly recited in the claims.

In some embodiments, components of the system described above may be made by injection molding, compression molding, blow molding, thermoforming, die pressing, slip casting, electrochemical machining, laser cutting, water-jet machining, electrophoretic deposition, powder injection molding, sand casting, shell mold casting, plaster-mold casting, investment casting, vacuum casting, permanent-mold casting, slush casting, pressure casting, die casting, centrifugal casting, squeeze casting, rolling, forging, swaging, extrusion, shearing, spinning, or combinations thereof.

In some embodiments, the components of the system may be formed by 3D printing. The terms "three-dimensional printing system," "three-dimensional printer," and "printing," describe various solid freeform fabrication techniques for making three-dimensional articles or objects by selective deposition, jetting, fused deposition modeling, multi-jet modeling, and other additive manufacturing techniques now known in the art or that may be known in the future that use a build material or ink to fabricate three-dimensional objects.

Instructions in the form of schematics encompassing any of the embodiments disclosed herein may be given to a computer to be carried out by a 3D printer. In some embodiments, components of the system may be color coded to signify various properties.

Components of the system may be sterilizable. In various embodiments, one or more components of the system are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the system. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the system, including, but not limited to, gas sterilization, such as, for example, with ethylene oxide or steam sterilization.

In various embodiments, a kit or system is provided that may include additional parts along with the cover combined together to be used with the tray. The kit may include the cover in a first compartment. A second compartment may include the tray. A third compartment may include a liner. A fourth compartment may include an additional cover. A fifth compartment may include gloves and other procedural supplies for maintaining sterility, as well as an instruction booklet or notification of a website where instructions for using the kit or system can be located. Each component of the system or kit may be separately packaged in a plastic pouch. A cover of the kit may include illustrations of the use of the cover and a clear plastic cover may be placed over the compartments to maintain sterility.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. An endoscope storage system, the system comprising an endoscope storage tray; a cover comprising a flexible and deformable sheet material configured to be temporarily secured to the endoscope storage tray and configured to partially enclose the endoscope storage tray; and a one-way valve attached to the cover; wherein, the endoscope storage system is configured to supply forced filtered air into the endoscope storage tray; and the one-way valve is configured to open in response to air pressure caused by the forced filtered air and prevents the cover from being detached from the endoscope storage tray.

2. The system of claim 1, wherein the one-way valve is a pressure valve and comprises an inlet, an outlet and a seal.

3. The system of claim 1, wherein the cover is a disposable single use cover, and the cover is a red, green or clear color to indicate that the endoscope is clean and ready for use.

4. The system of claim 1, further comprising a liner configured to engage the endoscope storage compartment of the endoscope storage tray.

5. The system of claim 4, wherein the liner contacts the storage compartment of the endoscope storage tray and an endoscope.

6. The system of claim 4, wherein the endoscope storage tray is a rigid and reusable tray.

7. The system of claim 4, the endoscope storage tray comprises an endoscope storage compartment comprising a planar base and surrounding walls upstanding therefrom.

8. The system of claim 7, further comprising a cart to store a plurality of endoscope storage trays.

9. The system of claim 8, wherein the cart and/or tray comprise an outlet configured to engage a working channel of the endoscope to receive forced filtered air.

10. The system of claim 8, further comprising an outlet member configured to engage a working channel of the endoscope to receive forced filtered air.

11. The system of claim 4, further comprising a basket, the basket disposed within the endoscope storage compartment.

12. The system of claim 11, wherein an endoscope is disposed within the basket, and an outlet member is configured to engage a working channel of the endoscope to receive forced filtered air.

13. The system of claim 4, further comprising a drying cabinet to store a plurality of endoscope storage trays.

14. The system of claim 13, wherein an endoscope is disposed within the drying cabinet, and an outlet member is configured to engage a working channel of the endoscope to receive forced filtered air.

15. The system of claim 1, further comprising an air source that utilizes a HEPA filter that is attached to an inlet defined by the endoscope storage tray.

16. A cover for an endoscope storage tray, the cover comprising a flexible and deformable sheet material; and a one-way valve attached to the cover, wherein the one-way valve is configured to open in response to pressure supplied by a forced filtered air sourcethat is connected to an endoscope; such that while the air source is active, the cover can be retained on the endoscope storage tray.

17. The cover of claim 16, wherein the cover is a disposable single use cover, and the cover is a red, green or clear color to indicate that the endoscope is clean and ready for use.

18. The cover of claim 16, further comprising an outlet member configured to engage a working channel of the endoscope to receive force filtered air.

19. The cover of claim 16, wherein the cover is substantially impermeable to fluids and is configured to be temporarily secured to the endoscope storage tray.

* * * * *